US012678307B2

(12) United States Patent (10) Patent No.: US 12,678,307 B2

Elwood et al. (45) Date of Patent: Jul. 14, 2026

(54) TRANSLUMINAL DELIVERY DEVICES AND RELATED KITS AND METHODS

(71) Applicant: Merit Medical Systems, Inc., South Jordan, UT (US)

(72) Inventors: Bryan K. Elwood, Arlington, TX (US); Thomas Patrick Robinson, Addison, TX (US); Zeke Eller, Plano, TX (US); John Twomey, Longmont, CO (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 18/301,717

(22) Filed: Apr. 17, 2023

(65) Prior Publication Data

US 2023/0381003 A1 Nov. 30, 2023

Related U.S. Application Data

(63) Continuation of application No. 15/921,220, filed on Mar. 14, 2018, now Pat. No. 11,628,078.

(Continued)

(51) Int. Cl.
*A61F 2/95* (2013.01)
*A61B 1/00* (2006.01)
(Continued)

(52) U.S. Cl.
CPC .............. *A61F 2/95* (2013.01); *A61B 1/0014* (2013.01); *A61B 1/018* (2013.01);
(Continued)

(58) Field of Classification Search
CPC .................. A61B 1/0014; A61B 1/018; A61B 17/320016; A61B 17/32053; A61B 17/3468; A61B 2017/00278; A61B 2017/0034; A61B 2017/00424; A61B 18/1492; A61B 2018/00077; A61B 2018/00083; A61B 2018/00178;

(Continued)

(56) References Cited

U.S. PATENT DOCUMENTS

| 3,115,138 A | 12/1963 | Mcelvenny et al. |
| 3,875,941 A | 4/1975 | Adair |

(Continued)

FOREIGN PATENT DOCUMENTS

| CN | 210185778 | 3/2020 |
| DE | 9209908 U1 | 9/1992 |

(Continued)

OTHER PUBLICATIONS

European Examination Report dated Feb. 2, 2023 for EP18768455. 0.

(Continued)

*Primary Examiner* — Khadijeh A Vahdat

(74) *Attorney, Agent, or Firm* — Dorsey & Whitney LLP

(57) ABSTRACT

Prosthesis deployment devices are disclosed herein. In some embodiments, the prosthesis deployment device comprises an elongate delivery catheter assembly configured for electrosurgery and also configured to retain and deploy a prosthesis. Kits comprising the prosthesis deployment devices with a prosthesis loaded into a prosthesis pod of the device are disclosed herein as well as methods of using the prosthesis deployment devices.

20 Claims, 26 Drawing Sheets

Related U.S. Application Data

(60) Provisional application No. 62/471,767, filed on Mar. 15, 2017.

(51) Int. Cl.

| | |
|---|---|
| *A61B 1/018* | (2006.01) |
| *A61B 17/34* | (2006.01) |
| *A61B 8/12* | (2006.01) |
| *A61B 17/00* | (2006.01) |
| *A61B 17/32* | (2006.01) |
| *A61B 17/3205* | (2006.01) |
| *A61B 18/00* | (2006.01) |
| *A61B 18/12* | (2006.01) |
| *A61B 18/14* | (2006.01) |
| *A61F 2/90* | (2013.01) |
| *A61M 25/00* | (2006.01) |
| *A61M 25/09* | (2006.01) |

(52) U.S. Cl.

CPC ............ *A61B 17/3468* (2013.01); *A61B 8/12* (2013.01); *A61B 2017/00278* (2013.01); *A61B 2017/0034* (2013.01); *A61B 2017/00424* (2013.01); *A61B 17/320016* (2013.01); *A61B 17/32053* (2013.01); *A61B 2018/00077* (2013.01); *A61B 2018/00083* (2013.01); *A61B 2018/00178* (2013.01); *A61B 2018/00601* (2013.01); *A61B 2018/00982* (2013.01); *A61B 2018/126* (2013.01); *A61B 18/1492* (2013.01); *A61F 2/90* (2013.01); *A61F 2/9517* (2020.05); *A61F 2230/001* (2013.01); *A61M 25/0082* (2013.01); *A61M 25/09* (2013.01)

(58) Field of Classification Search

CPC   A61B 2018/00601; A61B 2018/00982; A61B 2018/126

See application file for complete search history.

(56)                   References Cited

U.S. PATENT DOCUMENTS

| | | | |
|---|---|---|---|
| 3,991,763 A | 11/1976 | Genese |
| 4,029,095 A | 6/1977 | Pena |
| 4,122,851 A | 10/1978 | Grossner |
| 4,139,130 A | 2/1979 | Glusker et al. |
| 4,265,381 A | 5/1981 | Muscatell |
| 4,429,693 A | 2/1984 | Blake et al. |
| 4,435,171 A | 3/1984 | Goldberg et al. |
| 4,511,358 A | 4/1985 | Johnson, Jr. et al. |
| 4,529,402 A | 7/1985 | Weilbacher et al. |
| 4,569,674 A | 2/1986 | Phillips et al. |
| 4,582,508 A | 4/1986 | Pavelka |
| 4,583,972 A | 4/1986 | Hunter, III et al. |
| 4,642,088 A | 2/1987 | Gunter |
| 4,666,432 A | 5/1987 | McNeish et al. |
| 4,850,955 A | 7/1989 | Newkirk |
| 4,904,245 A | 2/1990 | Chen et al. |
| 4,913,141 A | 4/1990 | Hillstead |
| 4,981,474 A | 1/1991 | Bopp et al. |
| 5,019,059 A | 5/1991 | Goldberg et al. |
| 5,067,950 A | 11/1991 | Broadnax, Jr. |
| 5,087,251 A | 2/1992 | Heyman et al. |
| 5,201,757 A | 4/1993 | Heyn et al. |
| 5,313,938 A | 5/1994 | Garfield et al. |
| 5,413,575 A | 5/1995 | Haenggi |
| 5,425,719 A | 6/1995 | Lessing, Jr. |
| 5,472,325 A | 12/1995 | Svendsen |
| 5,496,299 A | 3/1996 | Felix et al. |
| 5,534,007 A | 7/1996 | Germain et al. |
| 5,591,172 A | 1/1997 | Bachmann et al. |
| 5,591,196 A | 1/1997 | Marin et al. |
| 5,603,698 A | 2/1997 | Roberts et al. |
| 5,645,559 A | 7/1997 | Hachtman et al. |

| | | | |
|---|---|---|---|
| 5,733,325 A | 3/1998 | Robinson et al. |
| 5,735,301 A | 4/1998 | Rower |
| 5,755,769 A | 5/1998 | Richard et al. |
| 5,759,186 A | 6/1998 | Bachmann et al. |
| 5,824,041 A | 10/1998 | Lenker et al. |
| 5,868,755 A | 2/1999 | Kanner et al. |
| 5,876,448 A | 3/1999 | Thompson et al. |
| 5,916,147 A | 6/1999 | Boury |
| 5,944,727 A | 8/1999 | Ahari et al. |
| 5,968,052 A | 10/1999 | Sullivan, III et al. |
| 5,980,499 A | 11/1999 | Ekey |
| 6,015,429 A | 1/2000 | Au et al. |
| 6,093,194 A | 7/2000 | Mikus et al. |
| 6,099,511 A | 8/2000 | Devos et al. |
| 6,123,715 A | 9/2000 | Amplatz |
| 6,143,021 A | 11/2000 | Staehle |
| 6,146,415 A | 11/2000 | Fitz |
| 6,162,231 A | 12/2000 | Mikus et al. |
| 6,241,757 B1 | 6/2001 | An et al. |
| 6,261,276 B1 | 7/2001 | Reitsma |
| 6,270,524 B1 | 8/2001 | Kim |
| 6,283,992 B1 | 9/2001 | Hankh et al. |
| 6,368,339 B1 | 4/2002 | Amplatz |
| 6,383,211 B1 | 5/2002 | Staehle |
| 6,391,051 B2 | 5/2002 | Sullivan, III et al. |
| 6,413,269 B1 | 7/2002 | Bui et al. |
| 6,416,545 B1 | 7/2002 | Mikus et al. |
| 6,428,566 B1 | 8/2002 | Holt |
| 6,443,980 B1 | 9/2002 | Wang et al. |
| 6,447,531 B1 | 9/2002 | Amplatz |
| 6,461,319 B1 | 10/2002 | Ekey |
| 6,514,261 B1 | 2/2003 | Randall et al. |
| 6,520,983 B1 | 2/2003 | Colgan et al. |
| 6,530,933 B1 | 3/2003 | Yeung et al. |
| 6,574,800 B1 | 6/2003 | Leger et al. |
| 6,599,296 B1 | 7/2003 | Gillick et al. |
| 6,599,308 B2 | 7/2003 | Amplatz |
| 6,610,032 B1 | 8/2003 | Prody |
| 6,613,079 B1 | 9/2003 | Wolinsky et al. |
| 6,616,675 B1 | 9/2003 | Evard et al. |
| 6,620,132 B1 | 9/2003 | Skow |
| 6,629,981 B2 | 10/2003 | Dennis et al. |
| 6,645,143 B2 | 11/2003 | Vantassel et al. |
| 6,669,719 B2 | 12/2003 | Wallace et al. |
| 6,726,712 B1 | 4/2004 | Raeder-Devens et al. |
| 6,740,068 B1 | 5/2004 | Aruffo et al. |
| 6,746,480 B2 | 6/2004 | Scholz et al. |
| 6,770,101 B2 | 8/2004 | Desmond, III et al. |
| 6,776,791 B1 | 8/2004 | Jody et al. |
| 6,821,295 B1 | 11/2004 | Farrar |
| 6,866,669 B2 | 3/2005 | Buzzard et al. |
| 6,887,223 B2 | 5/2005 | Bisbee |
| 6,893,413 B2 | 5/2005 | Martin |
| 6,926,732 B2 | 8/2005 | Derus et al. |
| 6,955,685 B2 | 10/2005 | Escamilla et al. |
| 7,004,966 B2 | 2/2006 | Edwin et al. |
| 7,083,640 B2 | 8/2006 | Lombardi et al. |
| 7,309,350 B2 | 12/2007 | Landreville et al. |
| 7,309,351 B2 | 12/2007 | Escamilla et al. |
| 7,335,224 B2 | 2/2008 | Ohlenschaeger |
| 7,393,357 B2 | 7/2008 | Stelter et al. |
| 7,473,271 B2 | 1/2009 | Gunderson |
| 7,591,848 B2 | 9/2009 | Allen |
| 7,637,942 B2 | 12/2009 | Mangiardi et al. |
| 7,661,152 B2 | 2/2010 | Manzano-Rivera |
| 7,731,654 B2 | 6/2010 | Mangiardi et al. |
| 7,766,886 B2 | 8/2010 | Garcia et al. |
| 7,823,221 B2 | 11/2010 | Green |
| 7,942,856 B2 | 5/2011 | Lentini |
| 7,959,671 B2 | 6/2011 | Mangiardi et al. |
| 7,976,521 B2 | 7/2011 | Hara et al. |
| 8,012,194 B2 | 9/2011 | Edwin et al. |
| 8,066,657 B2 | 11/2011 | Frazer |
| 8,206,436 B2 | 6/2012 | Mangiardi et al. |
| 8,226,621 B2 | 7/2012 | Timmons |
| 8,235,939 B2 | 8/2012 | Johnson et al. |
| 8,262,719 B2 | 9/2012 | Erickson et al. |
| 8,292,860 B1 | 10/2012 | Persichetti et al. |
| 8,348,914 B2 | 1/2013 | Zyburt et al. |

(56) References Cited

U.S. PATENT DOCUMENTS

| | | | |
|---|---|---|---|
| 8,357,193 | B2 | 1/2013 | Phan et al. |
| 8,366,690 | B2 | 2/2013 | Locke et al. |
| 8,414,635 | B2 | 4/2013 | Hyodoh et al. |
| 8,425,539 | B2 | 4/2013 | Binmoeller et al. |
| 8,439,934 | B2 | 5/2013 | Satasiya et al. |
| 8,454,632 | B2 | 6/2013 | Binmoeller et al. |
| 8,518,099 | B2 | 8/2013 | Chanduszko et al. |
| 8,524,132 | B2 | 9/2013 | Von Oepen et al. |
| 8,535,366 | B2 | 9/2013 | Mangiardi et al. |
| 8,636,721 | B2 | 1/2014 | Alam et al. |
| 8,641,692 | B2 | 2/2014 | Tout et al. |
| 8,652,099 | B2 | 2/2014 | Fierens et al. |
| 8,677,874 | B2 | 3/2014 | Lilburn et al. |
| 8,696,611 | B2 | 4/2014 | Yaacov et al. |
| 8,715,334 | B2 | 5/2014 | Clerc et al. |
| 8,814,839 | B2 | 8/2014 | Christensen et al. |
| 8,834,558 | B2 | 9/2014 | Nissl |
| 8,906,081 | B2 | 12/2014 | Cully et al. |
| 8,926,683 | B2 | 1/2015 | Darla et al. |
| 8,961,448 | B2 | 2/2015 | Forsell |
| 8,992,492 | B2 | 3/2015 | Anderson et al. |
| 9,155,643 | B2 | 10/2015 | Clerc et al. |
| 9,192,496 | B2 | 11/2015 | Robinson |
| 9,259,336 | B2 | 2/2016 | Schaeffer et al. |
| 9,284,637 | B2 | 3/2016 | Boyle et al. |
| 9,381,041 | B2 | 7/2016 | Brown et al. |
| 10,285,834 | B2 | 5/2019 | Cindrich et al. |
| 10,349,944 | B2 | 7/2019 | Han et al. |
| 2001/0037141 | A1 | 11/2001 | Yee et al. |
| 2002/0068037 | A1 | 6/2002 | Platzet et al. |
| 2002/0099435 | A1 | 7/2002 | Stinson |
| 2002/0138095 | A1 | 9/2002 | Mazzocchi et al. |
| 2002/0151967 | A1 | 10/2002 | Mikus et al. |
| 2002/0183827 | A1 | 12/2002 | Derus et al. |
| 2002/0193749 | A1 | 12/2002 | Olovson |
| 2003/0023268 | A1 | 1/2003 | Lizardi |
| 2003/0028236 | A1 | 2/2003 | Gillick |
| 2003/0050686 | A1 | 3/2003 | Raeder-Devens et al. |
| 2003/0135265 | A1 | 7/2003 | Stinson |
| 2003/0135268 | A1 | 7/2003 | Desai |
| 2003/0144671 | A1 | 7/2003 | Brooks et al. |
| 2003/0163101 | A1 | 8/2003 | Say |
| 2003/0167060 | A1 | 9/2003 | Buzzard et al. |
| 2004/0030381 | A1 | 2/2004 | Shu |
| 2004/0098077 | A1 | 5/2004 | Gianotti |
| 2004/0106977 | A1 | 6/2004 | Sullivan et al. |
| 2004/0127973 | A1 | 7/2004 | Mangiardi et al. |
| 2004/0181239 | A1 | 9/2004 | Dorn et al. |
| 2004/0193243 | A1 | 9/2004 | Mangiardi et al. |
| 2004/0267281 | A1 | 12/2004 | Harari et al. |
| 2005/0004447 | A1 | 1/2005 | Yamamoto |
| 2005/0027345 | A1 | 2/2005 | Horan et al. |
| 2005/0038495 | A1 | 2/2005 | Greenan |
| 2005/0090887 | A1 | 4/2005 | Pryor |
| 2005/0113902 | A1 | 5/2005 | Geiser et al. |
| 2005/0125050 | A1 | 6/2005 | Carter et al. |
| 2005/0149160 | A1 | 7/2005 | McFerran |
| 2005/0182475 | A1 | 8/2005 | Jen et al. |
| 2005/0278010 | A1 | 12/2005 | Richardson |
| 2005/0283179 | A1 | 12/2005 | Lentz |
| 2006/0020321 | A1 | 1/2006 | Parker |
| 2006/0155368 | A1 | 7/2006 | Shin |
| 2006/0184224 | A1 | 8/2006 | Angel |
| 2006/0258972 | A1 | 11/2006 | Mangiardi et al. |
| 2006/0259113 | A1 | 11/2006 | Nissl |
| 2007/0002122 | A1 | 1/2007 | Murano et al. |
| 2007/0005122 | A1 | 1/2007 | Inoue |
| 2007/0043421 | A1 | 2/2007 | Mangiardi et al. |
| 2007/0100421 | A1 | 5/2007 | Griffin |
| 2007/0135904 | A1 | 6/2007 | Eidenschink et al. |
| 2007/0156225 | A1 | 7/2007 | George et al. |
| 2007/0179590 | A1 | 8/2007 | Lu et al. |
| 2007/0208350 | A1 | 9/2007 | Gunderson |
| 2007/0250150 | A1 | 10/2007 | Pal et al. |
| 2007/0270932 | A1 | 11/2007 | Headley et al. |
| 2008/0097572 | A1 | 4/2008 | Sheldon et al. |
| 2008/0108948 | A1 | 5/2008 | Beaver |
| 2008/0114443 | A1 | 5/2008 | Mitchell et al. |
| 2008/0140178 | A1 | 6/2008 | Rasmussen et al. |
| 2008/0177252 | A1 | 7/2008 | Isik |
| 2008/0228256 | A1 | 9/2008 | Erickson et al. |
| 2008/0288042 | A1 | 11/2008 | Purdy et al. |
| 2009/0099636 | A1 | 4/2009 | Chanduszko et al. |
| 2009/0099647 | A1 | 4/2009 | Glimsdale et al. |
| 2009/0118740 | A1 | 5/2009 | Mangiardi et al. |
| 2009/0143731 | A1 | 6/2009 | Guzman |
| 2009/0157158 | A1 | 6/2009 | Ondracek |
| 2009/0171427 | A1 | 7/2009 | Melsheimer et al. |
| 2009/0171433 | A1 | 7/2009 | Melsheimer |
| 2009/0187240 | A1 | 7/2009 | Clerc |
| 2009/0192518 | A1 | 7/2009 | Golden et al. |
| 2009/0264988 | A1 | 10/2009 | Mafi et al. |
| 2009/0292262 | A1 | 11/2009 | Adams et al. |
| 2010/0023032 | A1 | 1/2010 | Granja et al. |
| 2010/0023132 | A1 | 1/2010 | Imran |
| 2010/0030256 | A1 | 2/2010 | Dubrul et al. |
| 2010/0030321 | A1 | 2/2010 | Mach |
| 2010/0049295 | A1 | 2/2010 | Satasiya et al. |
| 2010/0057145 | A1 | 3/2010 | Bhatnagar et al. |
| 2010/0057185 | A1 | 3/2010 | Melsheimer et al. |
| 2010/0070016 | A1 | 3/2010 | Dorn |
| 2010/0145431 | A1 | 6/2010 | Wu et al. |
| 2010/0174227 | A1 | 7/2010 | Ramella et al. |
| 2010/0198333 | A1 | 8/2010 | Macatangay et al. |
| 2010/0252470 | A1 | 10/2010 | Ryan et al. |
| 2010/0274229 | A1 | 10/2010 | Duocastella Codina et al. |
| 2011/0004290 | A1 | 1/2011 | Bales, Jr. et al. |
| 2011/0015616 | A1 | 1/2011 | Straubinger et al. |
| 2011/0071623 | A1* | 3/2011 | Finch ................. A61B 17/0057 |
| | | | 623/2.11 |
| 2011/0082464 | A1 | 4/2011 | Douk et al. |
| 2011/0137396 | A1* | 6/2011 | Dorn ....................... A61F 2/966 |
| | | | 623/1.11 |
| 2011/0137400 | A1 | 6/2011 | Dorn et al. |
| 2011/0190710 | A1 | 8/2011 | Miyoshi |
| 2011/0190862 | A1 | 8/2011 | Bashiri et al. |
| 2011/0208296 | A1 | 8/2011 | Duffy et al. |
| 2011/0230863 | A1 | 9/2011 | Lentini |
| 2011/0257723 | A1* | 10/2011 | McNamara ...... A61B 17/00234 |
| | | | 623/1.11 |
| 2011/0264191 | A1 | 10/2011 | Rothstein |
| 2011/0288482 | A1 | 11/2011 | Farrell et al. |
| 2011/0307070 | A1 | 12/2011 | Clerc et al. |
| 2011/0313360 | A1 | 12/2011 | Lin |
| 2011/0319980 | A1 | 12/2011 | Ryan |
| 2012/0046729 | A1 | 2/2012 | Von Oepen et al. |
| 2012/0095567 | A1 | 4/2012 | Weisman et al. |
| 2012/0136426 | A1 | 5/2012 | Phan et al. |
| 2012/0197203 | A1 | 8/2012 | Nokes, Jr. et al. |
| 2012/0283679 | A1 | 11/2012 | Berish et al. |
| 2012/0290066 | A1 | 11/2012 | Nabulsi et al. |
| 2012/0296257 | A1 | 11/2012 | Van et al. |
| 2012/0303109 | A1 | 11/2012 | Okuma |
| 2012/0303112 | A1 | 11/2012 | Armstrong et al. |
| 2012/0310320 | A1 | 12/2012 | Gill et al. |
| 2012/0330402 | A1 | 12/2012 | Vad et al. |
| 2013/0018215 | A1 | 1/2013 | Snider et al. |
| 2013/0060205 | A1 | 3/2013 | Mansour et al. |
| 2013/0103163 | A1 | 4/2013 | Krimsky et al. |
| 2013/0110221 | A1 | 5/2013 | Campbell et al. |
| 2013/0116770 | A1 | 5/2013 | Robinson |
| 2013/0116771 | A1 | 5/2013 | Robinson |
| 2013/0116772 | A1 | 5/2013 | Robinson et al. |
| 2013/0158673 | A1 | 6/2013 | Toomey |
| 2013/0184833 | A1 | 7/2013 | Ryan et al. |
| 2013/0197623 | A1 | 8/2013 | Mchugo |
| 2013/0226114 | A1 | 8/2013 | Massi et al. |
| 2013/0231689 | A1 | 9/2013 | Binmoeller et al. |
| 2013/0245585 | A1 | 9/2013 | Letellier |
| 2013/0253546 | A1 | 9/2013 | Sander et al. |
| 2013/0274870 | A1 | 10/2013 | Lombardi et al. |
| 2013/0296814 | A1 | 11/2013 | Antholz |
| 2013/0304181 | A1 | 11/2013 | Green et al. |

(56) References Cited

U.S. PATENT DOCUMENTS

| | | | |
|---|---|---|---|
| 2013/0310833 A1* | 11/2013 | Brown ............... | A61B 17/3478 606/45 |
| 2014/0005767 A1 | 1/2014 | Glazier et al. | |
| 2014/0031735 A1 | 1/2014 | Zurovick | |
| 2014/0074065 A1 | 3/2014 | Muni et al. | |
| 2014/0074219 A1 | 3/2014 | Hingston et al. | |
| 2014/0155744 A1 | 6/2014 | Pameijer | |
| 2014/0162400 A1 | 6/2014 | Vail et al. | |
| 2014/0171863 A1 | 6/2014 | Blacker | |
| 2014/0194778 A1 | 7/2014 | Uziel et al. | |
| 2014/0196792 A1 | 7/2014 | Torres-Leon | |
| 2014/0236064 A1 | 8/2014 | Binmoeller et al. | |
| 2014/0243992 A1 | 8/2014 | Walsh et al. | |
| 2014/0249412 A1 | 9/2014 | Yamamoto | |
| 2014/0277573 A1 | 9/2014 | Gill et al. | |
| 2014/0288636 A1 | 9/2014 | Headley, Jr. et al. | |
| 2014/0303709 A1 | 10/2014 | Dwork | |
| 2014/0330305 A1 | 11/2014 | Rood et al. | |
| 2014/0336744 A1 | 11/2014 | Tani et al. | |
| 2014/0350694 A1 | 11/2014 | Behan | |
| 2014/0364959 A1 | 12/2014 | Attar et al. | |
| 2015/0066128 A1 | 3/2015 | Losordo et al. | |
| 2015/0100133 A1 | 4/2015 | Xie et al. | |
| 2015/0112377 A1 | 4/2015 | Arnone et al. | |
| 2015/0173919 A1 | 6/2015 | Baldwin | |
| 2015/0230955 A1 | 8/2015 | Farag Eells et al. | |
| 2015/0297880 A1 | 10/2015 | Ogawa et al. | |
| 2015/0313595 A1 | 11/2015 | Houshton et al. | |
| 2015/0313599 A1 | 11/2015 | Johnson et al. | |
| 2016/0032769 A1 | 2/2016 | Stutz et al. | |
| 2016/0081823 A1 | 3/2016 | Majercak | |
| 2016/0081832 A1 | 3/2016 | Hingston et al. | |
| 2016/0242846 A1 | 8/2016 | Brown et al. | |
| 2016/0256306 A1 | 9/2016 | Cindrich et al. | |
| 2016/0310302 A1 | 10/2016 | Neglen et al. | |
| 2017/0014133 A1 | 1/2017 | Han et al. | |
| 2017/0035424 A1 | 2/2017 | Binmoeller et al. | |
| 2017/0035426 A1 | 2/2017 | Phan et al. | |
| 2017/0035427 A1 | 2/2017 | Sander et al. | |
| 2017/0035428 A1 | 2/2017 | Binmoeller et al. | |
| 2017/0049596 A1 | 2/2017 | Schabert | |
| 2017/0112624 A1 | 4/2017 | Patel | |
| 2017/0335152 A1 | 11/2017 | Botros | |
| 2017/0354404 A1 | 12/2017 | Chu | |
| 2018/0008248 A1 | 1/2018 | Rafiee et al. | |
| 2018/0014954 A1* | 1/2018 | Bradway ................. | A61F 2/844 |
| 2018/0185183 A1 | 7/2018 | Christakis et al. | |
| 2018/0263797 A1 | 9/2018 | Eller et al. | |
| 2018/0303594 A1 | 10/2018 | Eller et al. | |
| 2019/0044174 A1 | 2/2019 | Zhu et al. | |
| 2019/0099589 A1 | 4/2019 | Walsh et al. | |
| 2020/0375768 A1 | 12/2020 | Eller et al. | |
| 2021/0137713 A1 | 5/2021 | Shin et al. | |
| 2021/0161692 A1 | 6/2021 | Mower et al. | |
| 2022/0023026 A1 | 1/2022 | Eller et al. | |
| 2022/0125608 A1 | 4/2022 | Ethridge et al. | |
| 2022/0211527 A1 | 7/2022 | Mower et al. | |
| 2023/0381000 A1 | 11/2023 | Eller et al. | |
| 2025/0235313 A1 | 7/2025 | Eller et al. | |
| 2025/0235314 A1 | 7/2025 | Eller et al. | |

FOREIGN PATENT DOCUMENTS

| | | |
|---|---|---|
| DE | 4323866 | 1/1994 |
| DE | 102005051469 | 4/2007 |
| EP | 0364420 | 4/1990 |
| EP | 0408245 | 1/1991 |
| EP | 0872220 | 10/1998 |
| EP | 1637092 | 3/2006 |
| EP | 2522316 | 11/2012 |
| GB | 2243786 | 9/1989 |
| JP | H10305050 A | 11/1998 |
| JP | 2013196867 A | 9/2013 |
| JP | 2016032769 A | 3/2016 |
| JP | WO2014162400 A1 | 2/2017 |
| WO | 1993022986 A1 | 11/1993 |
| WO | 199631174 | 10/1996 |
| WO | 200018330 | 4/2000 |
| WO | 2000078246 | 12/2000 |
| WO | 2002056798 | 7/2002 |
| WO | 2002087470 | 11/2002 |
| WO | 2003090644 | 11/2003 |
| WO | 2004030571 | 4/2004 |
| WO | 2005070095 | 8/2005 |
| WO | 2008042266 | 4/2008 |
| WO | 2010130297 | 11/2010 |
| WO | 2011067280 A1 | 6/2011 |
| WO | 2012007044 A1 | 1/2012 |
| WO | 2012062603 A1 | 5/2012 |
| WO | 2013045262 | 4/2013 |
| WO | 2013052528 | 4/2013 |
| WO | 2013066883 | 10/2013 |
| WO | 2015184154 | 12/2015 |
| WO | 2016141295 A1 | 9/2016 |
| WO | 2019099080 | 5/2019 |
| WO | 2020146261 | 7/2020 |

OTHER PUBLICATIONS

European Examination Report dated Feb. 18, 2015 for EP09791142.4.
European Examination Report dated Apr. 26, 2021 for EP11846358.7.
European Search Report dated Feb. 3, 2015 for EP12846255.3.
European Search Report dated Mar. 19, 2021 for EP18768455.0.
European Search Report dated Apr. 9, 2018 for EP15860892.7.
European Search Report dated Apr. 24, 2020 for EP17857414.1.
European Search Report dated May 4, 2007 for EP05705271.4.
European Search Report dated Jun. 30, 2017 for EP11846358.7.
European Search Report dated Nov. 9, 2020 for EP18767753.9.
European Search Report dated Dec. 15, 2020 for EP18768455.0.
European Search Reported Sep. 24, 2018 for EP16759580.
International Preliminary Report dated May 15, 2014 for PCT/US2012/062603.
International Publication and Search Report Jun. 14, 2012 for WO2012078794.
International Publication and Search Report dated Feb. 25, 2012 for WO2010021836.
International Publication and Search Report dated Aug. 4, 2005 for WO2005070095.
International Publication and Search Report dated Dec. 19, 2006 for WO2005070095.
International Search Report and Written Opinion dated Jan. 9, 2018 for PCT/US2017/054000.
International Search Report and Written Opinion dated Feb. 14, 2022 for PCT/US2021/056495.
International Search Report and Written Opinion dated Mar. 16, 2012 for PCT/US2011/063799.
International Search Report and Written Opinion dated Mar. 29, 2013 for PCT/US2012/062603.
International Search Report and Written Opinion dated May 10, 2013 for PCT/US2012/060364.
International Search Report and Written Opinion dated Jun. 22, 2016 for PCT/US2016/020900.
International Search Report and Written Opinion dated Jun. 29, 2018 for PCT/US2018/022340.
International Search Report and Written Opinion dated Jun. 29, 2018 for PCT/US2018/022344.
International Search Report and Written Opinion dated Aug. 2, 2018 for PCT/US2018/028107.
International Search Report and Written Opinion dated Sep. 12, 2016 for PCT/US2016/040174.
International Search Report and Written Opinion dated Sep. 28, 2005 for PCT/US2005/000515.
International Search Report and Written Opinion dated Oct. 29, 2009 for PCT/US2009/052691.
International Search Report and Written Opinion dated Nov. 9, 2021 for PCT/US2021/042833.

(56)        References Cited

OTHER PUBLICATIONS

International Search Report and Written Opinion dated Nov. 23, 2006 for PCT/US2006/018811.
Notice of Allowance dated Jan. 5, 2023 for U.S. Appl. No. 15/921,220.
Notice of Allowance dated Jan. 14, 2015 for U.S. Appl. No. 11/432,964.
Notice of Allowance dated Feb. 25, 2019 for U.S. Application No. 15/061, 107.
Notice of Allowance dated Mar. 6, 2013 for U.S. Appl. No. 12/535,980.
Notice of Allowance dated Mar. 15, 2023 for U.S. Appl. No. 16/994,260.
Notice of Allowance dated Jun. 11, 2013 for U.S. Appl. No. 10/585,430.
Notice of Allowance dated Jun. 22, 2016 for U.S. Appl. No. 13/664,267.
Notice of Allowance dated Jul. 22, 2020 for U.S. Appl. No. 15/718,419.
Notice of Allowance dated Aug. 12, 2015 for U.S. Appl. No. 13/664,200.
Notice of Allowance dated Sep. 6, 2018 for U.S. Appl. No. 29/597,873.
Notice of Allowance dated Sep. 11, 2019 for U.S. Appl. No. 15/263,741.
Notice of Allowance dated Sep. 23, 2016 for U.S. Appl. No. 13/664,234.
Notice of Allowance dated Oct. 21, 2014 for U.S. Appl. No. 13/313,929.
Office Action dated Jan. 3, 2014 for U.S. Appl. No. 11/432,964.
Office Action dated Jan. 22, 2013 for U.S. Appl. No. 10/585,430.
Office Action dated Apr. 16, 2024 for U.S. Appl. No. 17/068,521.
Office Action dated Oct. 3, 2023 for U.S. Appl. No. 17/068,521.
Office Action dated Jan. 31, 2012 for U.S. Appl. No. 10/585,430.
Office Action dated Feb. 5, 2020 for U.S. Appl. No. 15/921,172.
Office Action dated Mar. 6, 2020 for U.S. Appl. No. 15/955,895.
Office Action dated Mar. 16, 2015 for U.S. Appl. No. 13/664,234.
Office Action dated Mar. 22, 2016 for U.S. Appl. No. 13/664,234.
Office Action dated Mar. 24, 2015 for U.S. Appl. No. 13/664,267.
Office Action dated Apr. 6, 2016 for U.S. Appl. No. 13/664,137.
Office Action dated Apr. 7, 2020 for U.S. Appl. No. 15/955,895.
Office Action dated Apr. 15, 2022 for U.S. Appl. No. 15/921,220.
Office Action dated Apr. 23, 2020 for U.S. Appl. No. 15/596,823.
Office Action dated Apr. 25, 2018 for U.S. Appl. No. 15/061,107.
Office Action dated May 5, 2014 for U.S. Appl. No. 13/313,929.
Office Action dated May 21, 2021 for U.S. Appl. No. 15/921,220.
Office Action dated May 25, 2012 for U.S. Appl. No. 12/535,980.
Office Action dated May 30, 2019 for U.S. Appl. No. 15/263,741.
Office Action dated Jun. 7, 2011 for U.S. Appl. No. 10/585,430.
Office Action dated Jun. 23, 2020 for U.S. Appl. No. 15/696,440.

Office Action dated Jul. 9, 2009 for U.S. Appl. No. 11/432,964.
Office Action dated Jul. 25, 2013 for U.S. Appl. No. 11/432,964.
Office Action dated Aug. 13, 2012 for U.S. Appl. No. 10/585,430.
Office Action dated Sep. 19, 2018 for U.S. Appl. No. 15/061,107.
Office Action dated Oct. 7, 2015 for U.S. Appl. No. 13/664,234.
Office Action dated Oct. 16, 2015 for U.S. Appl. No. 13/664,267.
Office Action dated Oct. 16, 2017 for U.S. Appl. No. 15/061,107.
Office Action dated Oct. 16, 2019 for U.S. Appl. No. 15/596,823.
Office Action dated Nov. 9, 2010 for U.S. Appl. No. 10/585,430.
Office Action dated Nov. 9, 2021 for U.S. Appl. No. 15/921,221.
Office Action dated Nov. 14, 2012 for U.S. Appl. No. 12/535,980.
Office Action dated Nov. 14, 2018 for U.S. Appl. No. 15/263,741.
Office Action dated Nov. 19, 2015 for U.S. Appl. No. 13/664,137.
Office Action dated Nov. 25, 2022 for U.S. Appl. No. 16/994,260.
Office Action dated Nov. 30, 2016 for U.S. Appl. No. 13/664,137.
Office Action dated Dec. 2, 2019 for U.S. Appl. No. 15/718,419.
Office Action dated Dec. 7, 2009 for U.S. Appl. No. 11/432,964.
Office Action dated Dec. 8, 2009 for U.S. Appl. No. 10/585,430.
Office Action dated Dec. 22, 2020 for U.S. Appl. No. 15/921,220.
Cheon , et al., "Clinical Feasibility of a New Through-The-Scope Fully Covered Esophageal Self-Expandable Metallic Stent: an In Vivo Animal Study", Digestive Endoscopy, vol. 26 No. 1, Jan. 1, 2014, 32-36.
Kawakami , et al., "Endoscopic Ultrasound-Guided Transluminal Drainage for Peripancreatic Fluid Collections: Where are we now?", Gut and Liver, vol. 8 No. 4, Jan. 1, 2014, 341-355.
Sen , et al., "Laplace's Equation for Convective Scalar Transport in Potential Flow", Proc. R. Soc. Lond. A 456, pp. 3041-3045, Jan. 1, 2000.
Sizarov , et al., "Novel materials and Devices in the Transcatheter Creation of vascular Anastomosis - The Future Comes Slowly (Part 2)", Archives of Cardiovascular Diseases, vol. 109 No. 4, Jan. 1, 2016, 286-295.
Weilert , et al., "Specially Designed Stents for Translumenal Drainage", Gastrointestinal Intervention, vol. 4 No. 1, Jan. 1, 2015, 40-45.
European Search Report dated Nov. 5, 2024 for EP24175441.5.
Office Action dated Nov. 7, 2024 for U.S. Appl. No. 17/068,521.
Office Action dated Aug. 9, 2024 for U.S. Appl. No. 17/068,521.
Notice of Allowance dated Dec. 18, 2024 for U.S. Appl. No. 17/068,521.
European Search Report dated Feb. 5, 2025 for EP24194404.0.
International Search Report and Written Opinion dated May 12, 2025 for PCT/US2025/012605.
Office Action dated Apr. 3, 2025 for U.S. Appl. No. 17/655,846.
Office Action dated Jul. 18, 2025 for U.S. Appl. No. 17/665,846.
Office Action dated Jan. 15, 2026 for U.S. Appl. No. 17/655,846.
"Definition of Convex", https://www.collinsdictionary.com/us/dictionary/english/convex.
Office Action dated Mar. 26, 2026 for U.S. Appl. No. 18/327,410.
Office Action dated Apr. 29, 2026 for U.S. Appl. No. 17/655,846.

* cited by examiner

175

171

175i

176i

172i

170i

171i

TRANSLUMINAL DELIVERY DEVICES AND RELATED KITS AND METHODS

RELATED APPLICATIONS

This application is a continuation of U.S. application Ser. No. 15/921,220, filed on Mar. 14, 2018 and titled "Transluminal Delivery Devices and Related Kits and Methods," now U.S. Pat. No. 11,628,078, which claims priority to United States Provisional Application No. 62/471,767 filed Mar. 15, 2017, and titled "Transluminal Delivery Devices and Related Kits and Methods," both of which are hereby incorporated by reference in their entireties.

TECHNICAL FIELD

This application generally relates to medical devices. More particularly, this application relates to transluminal delivery devices and related kits and methods.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Prosthesis deployment devices are disclosed herein. In some embodiments, the prosthesis deployment device comprises an elongate delivery catheter assembly configured for electrosurgery and also configured to retain and deploy a prosthesis. The prosthesis deployment device may further comprise a housing assembly operably coupled to the delivery catheter assembly and configured to connect to an electrosurgical power generator. The housing assembly may comprise an actuator configured to displace a portion of the delivery catheter assembly to deploy the prosthesis, upon actuation. The actuator may be configured for one-handed operation.

Kits comprising the prosthesis deployment devices with a prosthesis loaded into a prosthesis pod of the device are disclosed herein as well as methods of using the prosthesis deployment devices.

It will be readily understood that the components of the embodiments as generally described and illustrated in the figures herein could be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrases "communication with," "engaged with," "connected to," and "coupled to" are used in their ordinary sense, and are broad enough to refer to any suitable coupling or other form of interaction between two or more entities, including mechanical, electrical, magnetic, electromagnetic, fluid, and thermal interaction. Two components may interact with each other even though they are not in direct contact with each other. For example, two components may be coupled to each other through an intermediate component. The directional terms "proximal" and "distal" are used herein to refer to opposite locations on a component or device. The proximal end of a component or device is defined as the end of the device closest to the practitioner when the device is in normal use by the practitioner. The distal end is the end opposite the proximal end, along the longitudinal direction of the device, or the end farthest from the practitioner during normal use.

Figure 1:
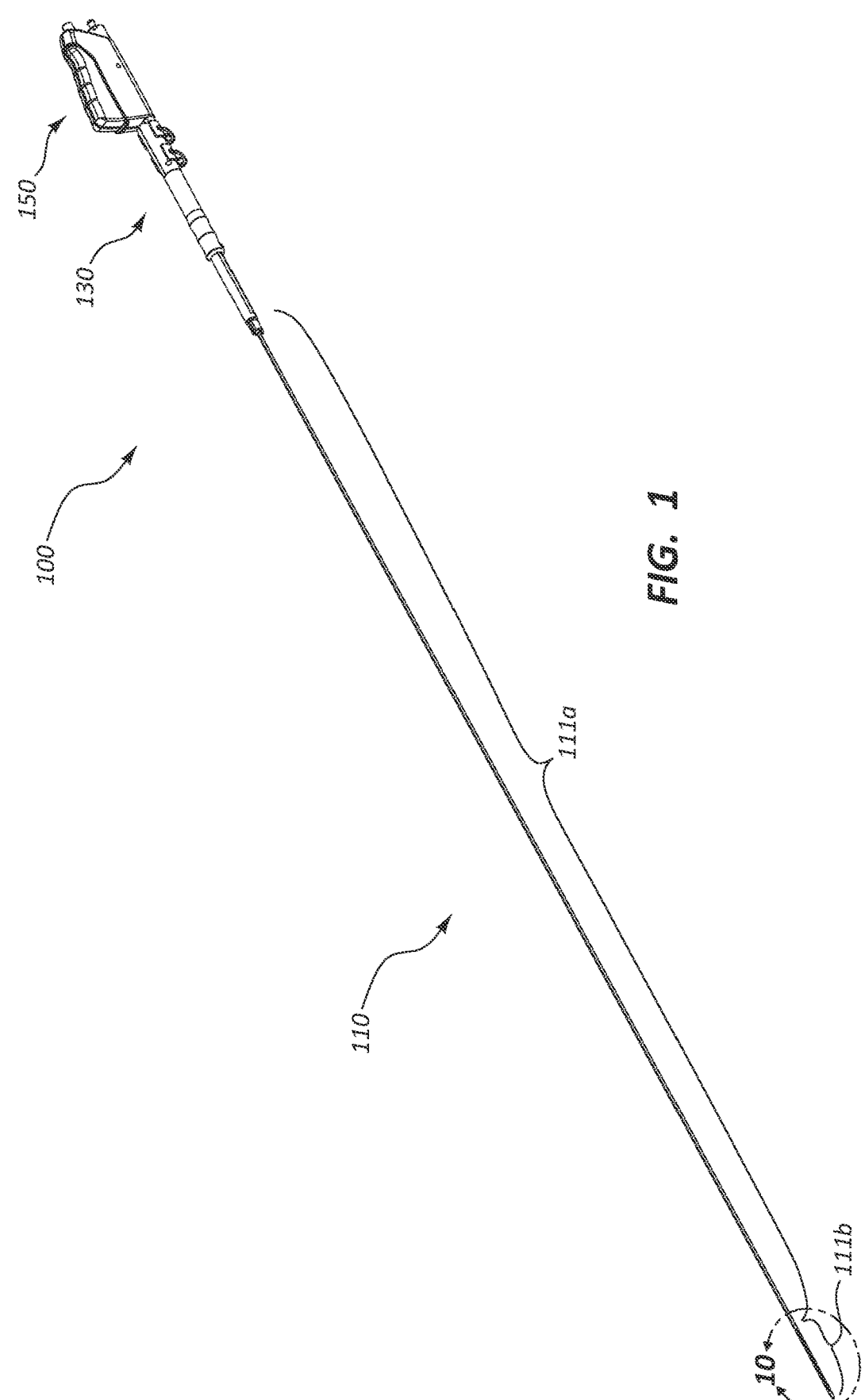
FIG. 1 illustrates an exemplary embodiment of a prosthesis delivery device.

Turning now to the figures, FIG. 1 illustrates an exemplary embodiment of a prosthesis delivery device 100. The prosthesis delivery device 100 includes an elongate delivery catheter assembly configured for electrosurgery and also configured to retain and deploy a prosthesis. The prosthesis delivery device 100 includes a housing assembly 130 operably coupled to the delivery catheter assembly 110 and configured to connect to an electrosurgical power generator (not shown). The housing assembly 130 includes a handle assembly 150 configured to displace a portion of the delivery catheter assembly 110 to deploy the prosthesis 200, upon actuation of the handle assembly 150. In the illustrated embodiment, the handle assembly 150 is configured for one-handed operation.

Figure 2A:
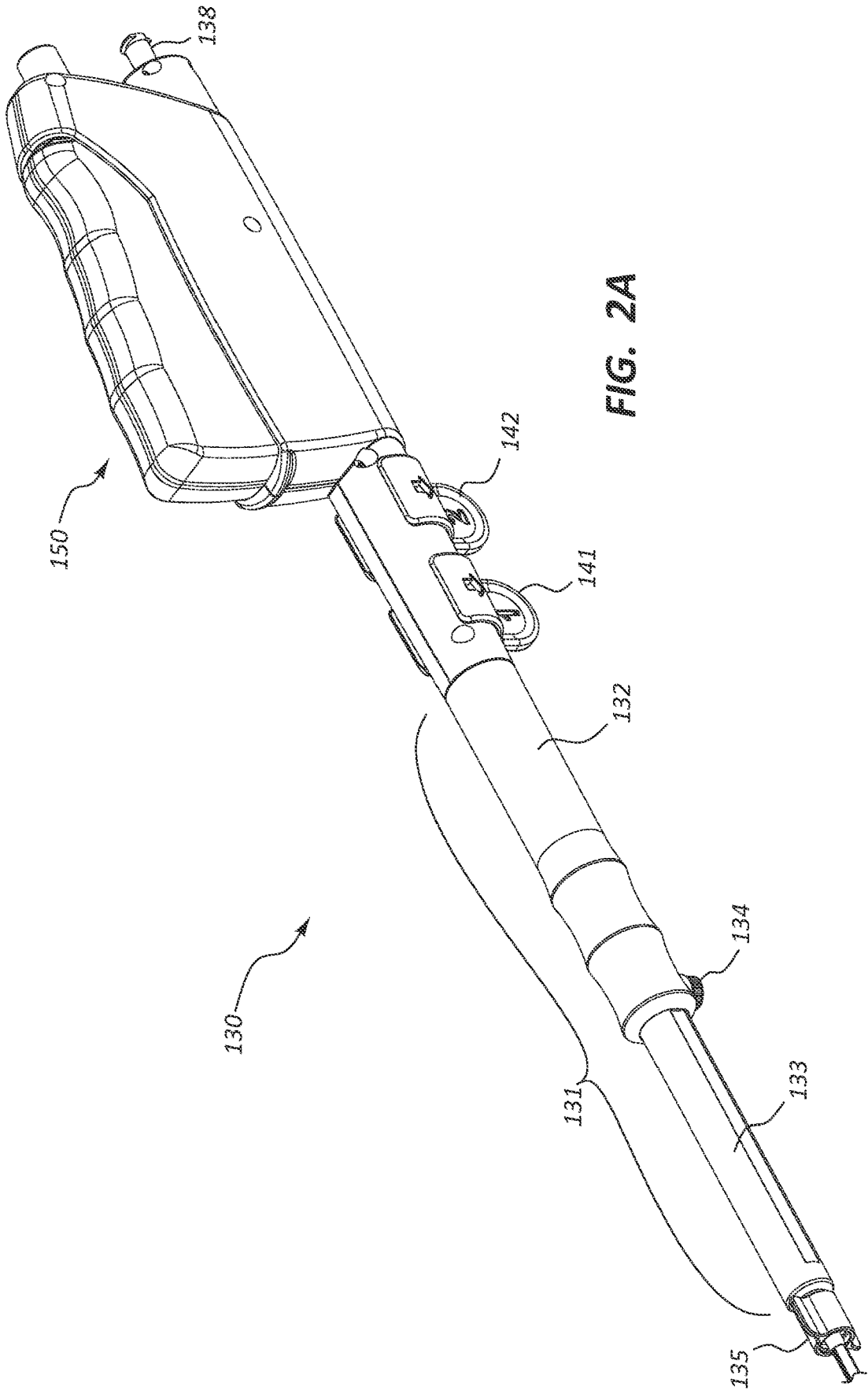
FIG. 2A illustrates a close-up perspective view of the housing assembly of the exemplary embodiment of FIG. 1 with the slide assembly fully extended.
Figure 2B:
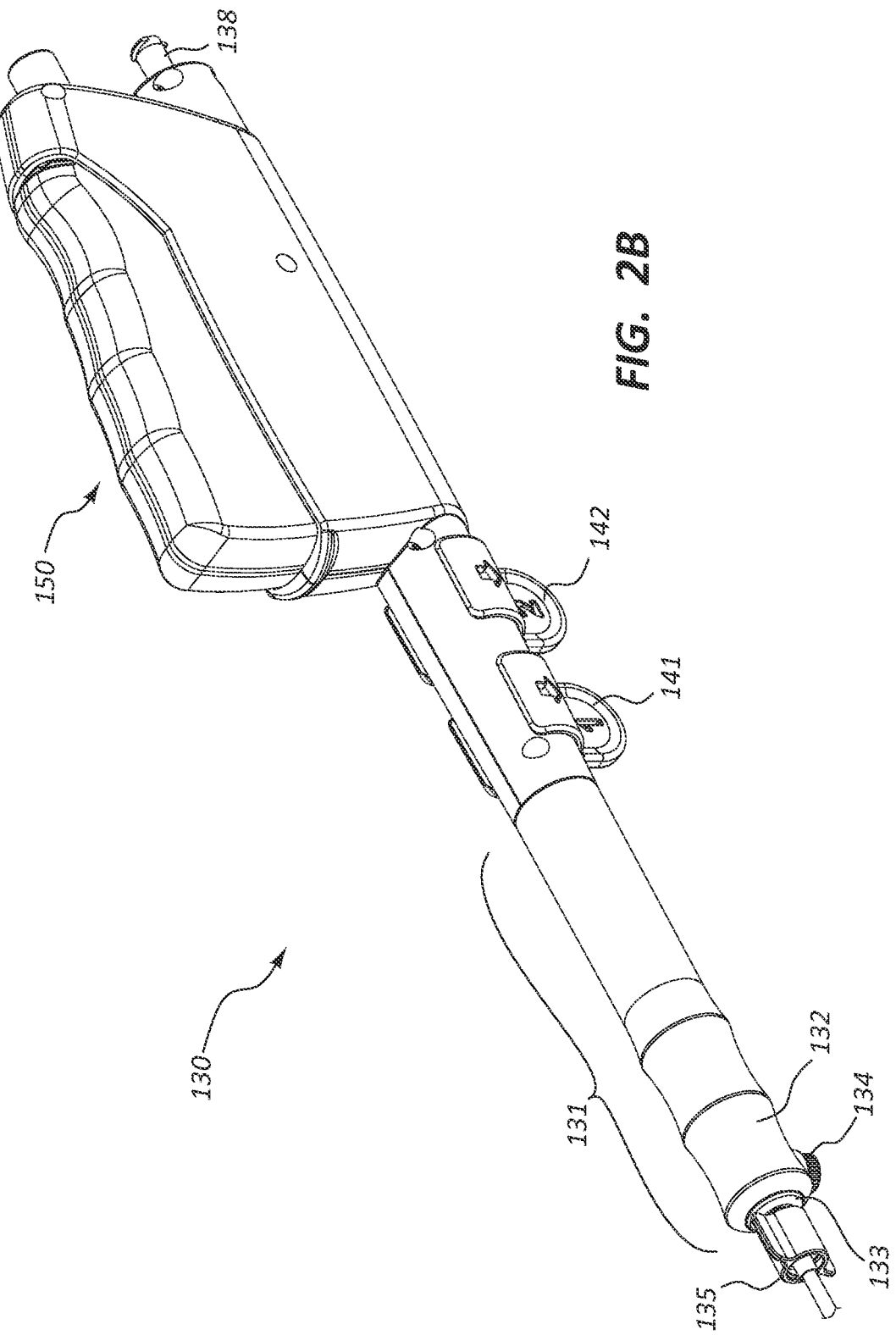
FIG. 2B illustrates a close-up perspective view of the housing assembly of the exemplary embodiment of FIG. 1 with the slide assembly fully contracted.

FIG. 2A illustrates a close-up perspective view of the housing assembly 130 with a slide assembly 131 fully extended. FIG. 2B illustrates a close-up perspective view of the housing assembly of the exemplary embodiment of FIG. 1 with the slide assembly 131 fully contracted. In the illustrated embodiment, the delivery catheter assembly 110 is configured for insertion in a working channel of an echoendoscope (not shown). Upon engagement with the echoendoscope (such as via rotatable male luer lock adapter 135), the slide assembly 131 is configured to allow adjustment of the position of the delivery catheter assembly 110 relative to the echoendoscope. For example, the tip electrode 170 may only extend slightly past the echoendoscope (referring to termination of the working channel) when the delivery catheter assembly 110 is fully inserted through the working channel. The slide assembly 131 may allow sufficient movement of the tip electrode 170 (discussed in more detail below) to perform electrosurgery and correct placement of the delivery catheter assembly 110 for deployment of the prosthesis 200. For example, when placing a 8 mm stent (mid-body length), the tip electrode 170 may need to extend 4 cm or more beyond the end of the echoendoscope.

Similarly, for a 20 mm stent, the tip electrode 170 may need to extend 10 cm or more beyond the end of the echoendoscope. The length of the slide assembly 131, in particular the length of the piston 133, can be selected to provide the necessary travel for the tip electrode 170 beyond the end of the echoendoscope.

The slide assembly 131 may be configured such that distal movement of the slide assembly 131 moves the delivery catheter assembly 110 in a distal direction and proximal movement of the slide assembly 131 moves the delivery catheter assembly 110 in a proximal direction. For example, in the embodiment illustrated in FIGS. 2A and 2B, the slide assembly 131 comprises a slide handle 132 configured to slide back and forth over a fixed piston 133. The slide assembly 131 also includes a thumbscrew 134. The lockable slide handle 132 is configured for one-handed operation. The slide handle 132 may include a variety of grip patterns to enhance the ease of grip by the user. A user grasping the slide handle 132 with the right hand (endoscopes are typically configured for left-handed operation) can rotate the thumbscrew 134 with the user's thumb (or thumb and index finger combination) to unlock the slide handle 132. The user can then, with only one hand, slide the slide handle 132 distally over the piston 133. The handle assembly 150 is coupled to the slide handle 132, such that movement of the slide handle 132 also moves the handle assembly 150 and the delivery catheter assembly 110 coupled thereto (discussed below in relation to FIG. 14). The slide handle 132 can slide over the piston 133 until it is fully contracted within the slide handle 132, such as illustrated in FIG. 2B. The slide handle 132 can also be proximally retracted and locked into place at any juncture along the piston 133. It should be understood that alternative locking mechanisms to the thumbscrew 134 are encompassed by this disclosure, such as depressible buttons and slidable switches.

A user may adjust the slide assembly 131 under endoscopic ultrasonography (EUS) guidance. An advantage of one-handed operation of the slide assembly 132 is that a user can be watching a video screen and meanwhile easily adjust the position of the delivery catheter assembly 110 with one hand, and still have the other hand (typically the left hand) free for endoscope-related operations.

Figure 3A:
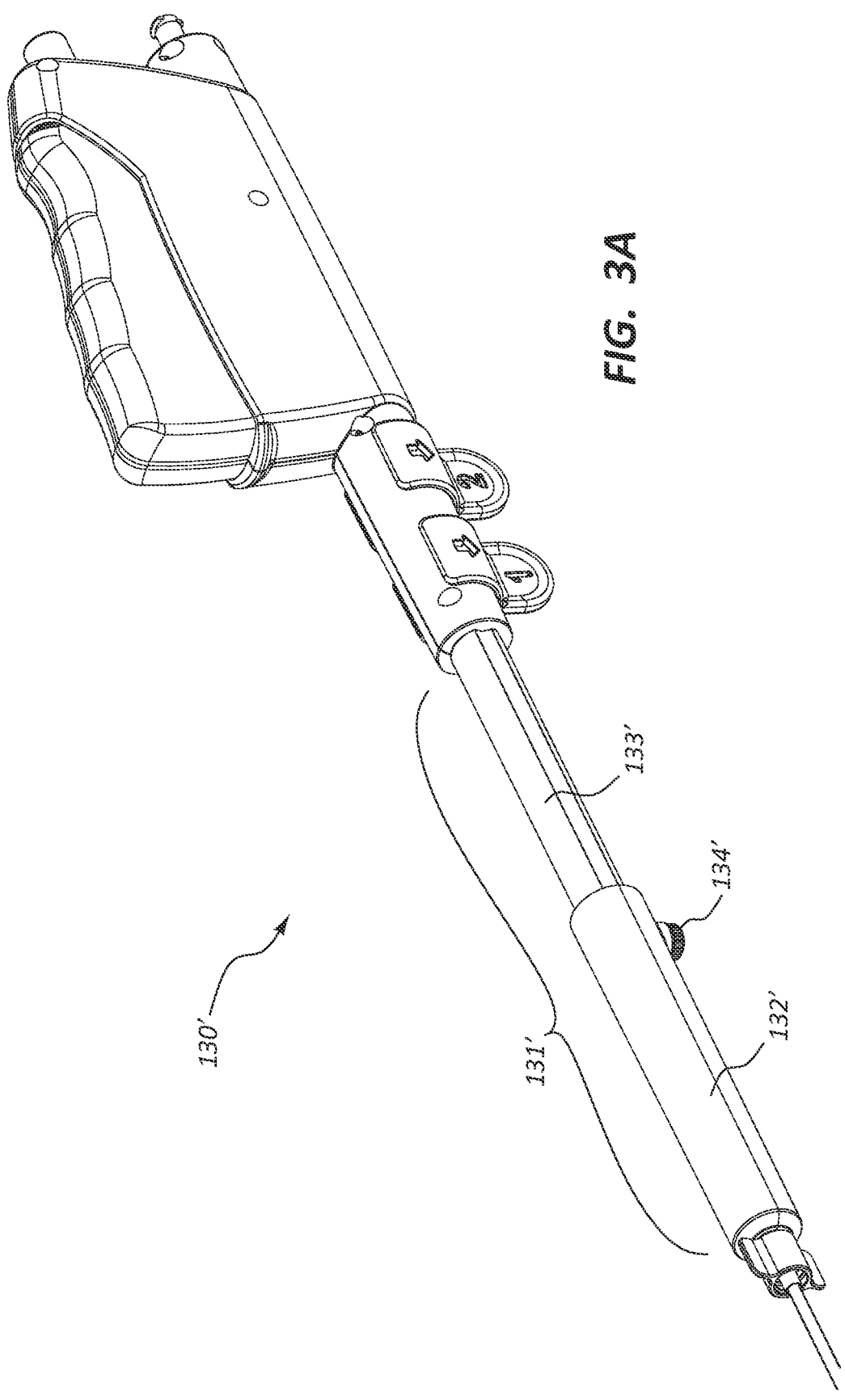
FIG. 3A illustrates a close-up perspective view of one embodiment of an alternative slide assembly, with the slide assembly fully extended.
Figure 3B:
FIG. 3B illustrates a close-up perspective view of the alternative slide assembly embodiment of FIG. 3A when fully contracted.

FIGS. 3A and 3B illustrate an alternative embodiment also configured for one-handed slide adjustment. FIG. 3A illustrates a close-up perspective view of a housing assembly 130' with an alternative slide assembly 131' in a fully extended state. FIG. 3B illustrates a close-up perspective view of the slide assembly 131' in a fully contracted state. In this embodiment, the slide assembly 131' comprises a fixed handle 132' and slidable piston 133'. The slide assembly 131' incudes a thumbscrew 134'. The handle assembly 150 is coupled to the piston 133', such that movement of the handle assembly 150, and the delivery catheter assembly 110 coupled thereto, moves the piston 133'. A user grasping the handle 132' with the right hand can rotate the thumbscrew 134' with the user's thumb (or thumb and index finger) to unlock the piston 133'. The user can then, with the same hand, grasp the handle assembly 150 and push the piston 133' into the handle 132'. Likewise, the same hand (or a second user's hand) can pull back on the handle assembly 150 to withdraw the piston 133' from the handle 132' and move the delivery catheter assembly 110 in the proximal direction. A difference between the slide assembly 131 and the alternative slide assembly 131' is that for the alternative slide assembly 131', a user must move his or her hand between unlocking the piston 133' and advancing or retracting the handle assembly 150.

Referring again to FIGS. 2A and 2B, in the illustrated embodiment, the housing assembly 130 comprises a rotatable male luer lock adapter 135 configured to mate with a female luer lock adapter (not shown) attached to the working channel of the echoendoscope. The rotatable male luer lock adapter 135 secures engagement of the housing assembly 130 to the working channel of the echoendoscope. The rotatable male luer lock adapter 135 is coupled to the piston 133.

Figure 4:
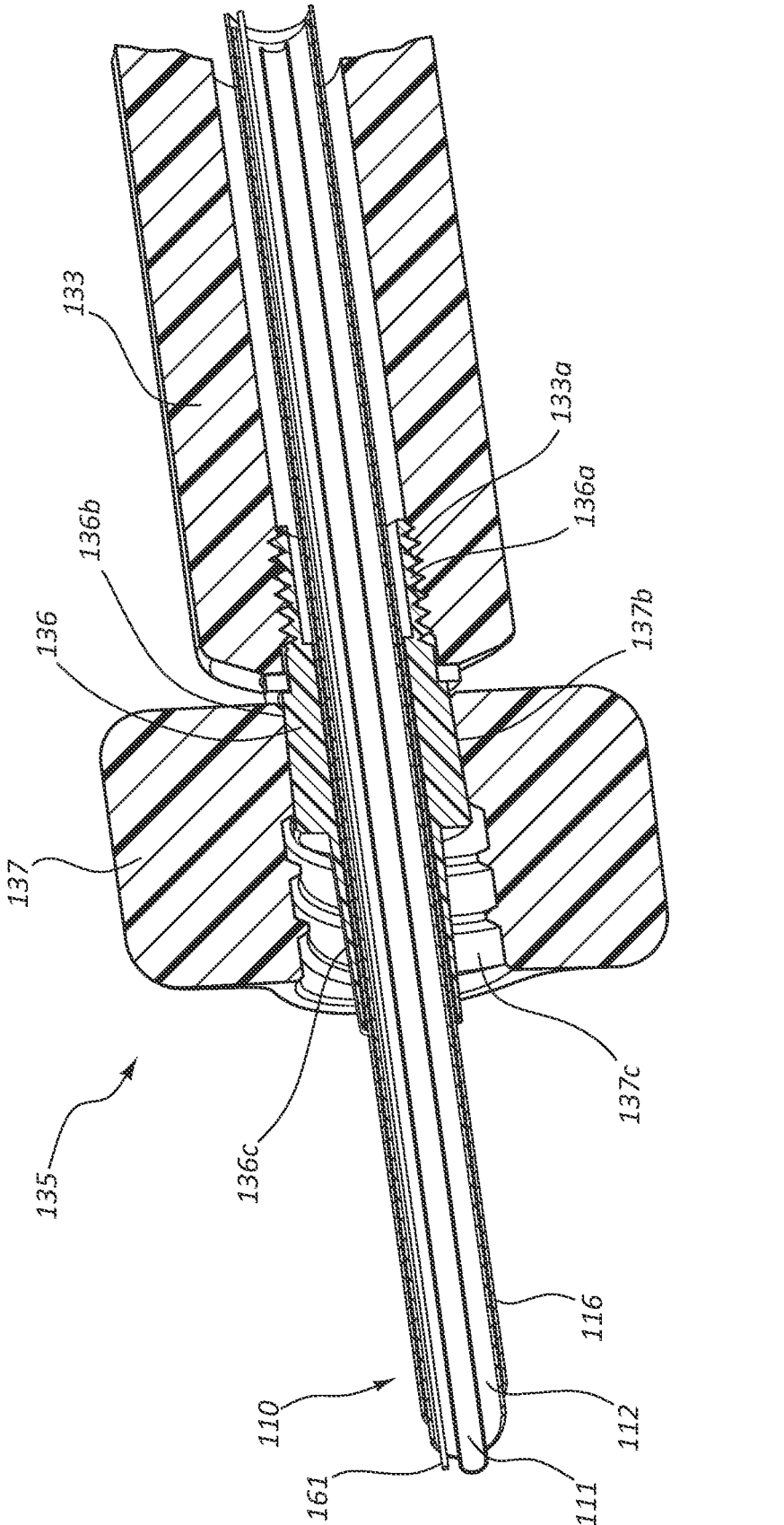
FIG. 4 illustrates a cross-sectional perspective view of a rotatable male luer lock adapter.

FIG. 4 illustrates a cross-sectional perspective view of the rotatable male luer lock adapter 135. The rotatable male luer lock adapter 135 comprises a fixed shank 136 and a rotatable housing 137. The fixed shank 136 has a threaded region 136a, a proximal outer taper 136b, and a distal outer taper 136c. The threaded region 136a is located proximal to the proximal outer taper 136b and threadingly engages threads 133a at the distal end of the piston 133. This secures the fixed shank 136 to the piston 133. The rotatable housing 137 has a proximal inner taper 137b and a distal inner threaded collar 137c. The proximal inner taper 137b is configured to rotate about the proximal outer taper 136b. The distal outer taper 136c is configured to mate with an inner surface of the female luer lock adapter (not shown). The distal inner threaded collar 137c is configured to mate with an outer lip of the female luer lock adapter (not shown), such that rotation of the rotatable housing 137 in a clockwise direction frictionally engages the distal outer taper 136c with the inner surface of the female luer lock adapter and also frictionally engages the proximal outer taper 136b with the proximal inner taper 137b, thereby securing the rotatable housing 137. In the illustrated embodiment, the proximal outer taper 136b and the distal outer taper 136c have equal and opposite angles from a profile perspective. For example, the proximal outer taper 136b and the distal outer taper 136c may each have a 6 percent taper. The fixed shank 136 and the rotatable housing 137 may be made of any material or combination of materials suitable for the intended use. For example, metallic threads may be used to provide sufficient strength, but rubber covers may be used to prevent electrical conduction via the rotatable male luer lock adapter 135.

Figure 15:
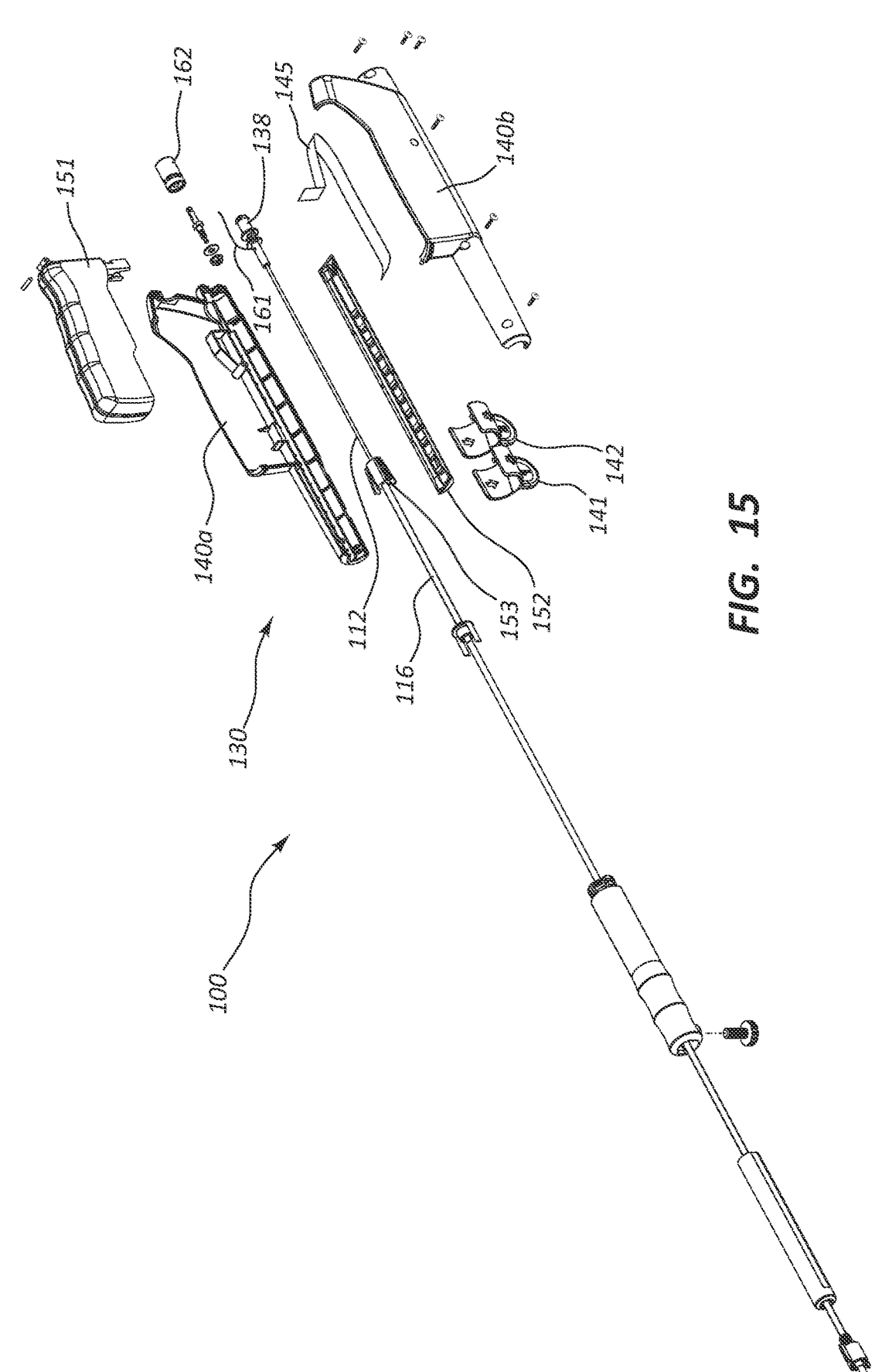
FIG. 15 illustrates an exploded view of the housing assembly of FIG. 1.

Referring to area 10 of FIG. 1, the catheter assembly 110 includes a tip electrode 170. The tip electrode 170 may be configured for monopolar or bipolar operation. In the illustrated embodiments, the tip electrode 170 is configured for monopolar operation, or in other words, the tip electrode 170 has a single active electrode and the second electrode for completing the circuit is a dispersive electrode (not shown) that is external to the prosthesis delivery device 100. Accordingly, a conductor 161 (see FIG. 4) runs the length of the prosthesis delivery device 100, there being no need for a second conductor as in bipolar operation. FIG. 15 illustrates electrical connection of the conductor 161 to an electrical connection 162. The electrical connection 162 is configured for monopolar connection to an electrosurgical power generator (not shown) and may include a 3 mm or 4 mm monopolar post, for example. Likewise, if the tip electrode 170 was configured for bipolar operation, the housing may comprises an electrical connection configured for bipolar connection to the electrosurgical power generator. For example, a second conductor in addition to conductor 161 may be present.

The tip electrode 170 may be configured to quickly cut through tissue walls, such as within about three seconds or less. The tip electrode 170 may be configured to have low friction as the tip electrode 170 is pushed through tissue walls, thereby reducing the force required for passage through the tissue walls. The surface area of the electrode portion of the tip electrode 170 may be minimized so as to focus the current density of the electrode portion.

Figures 5A, 5B:
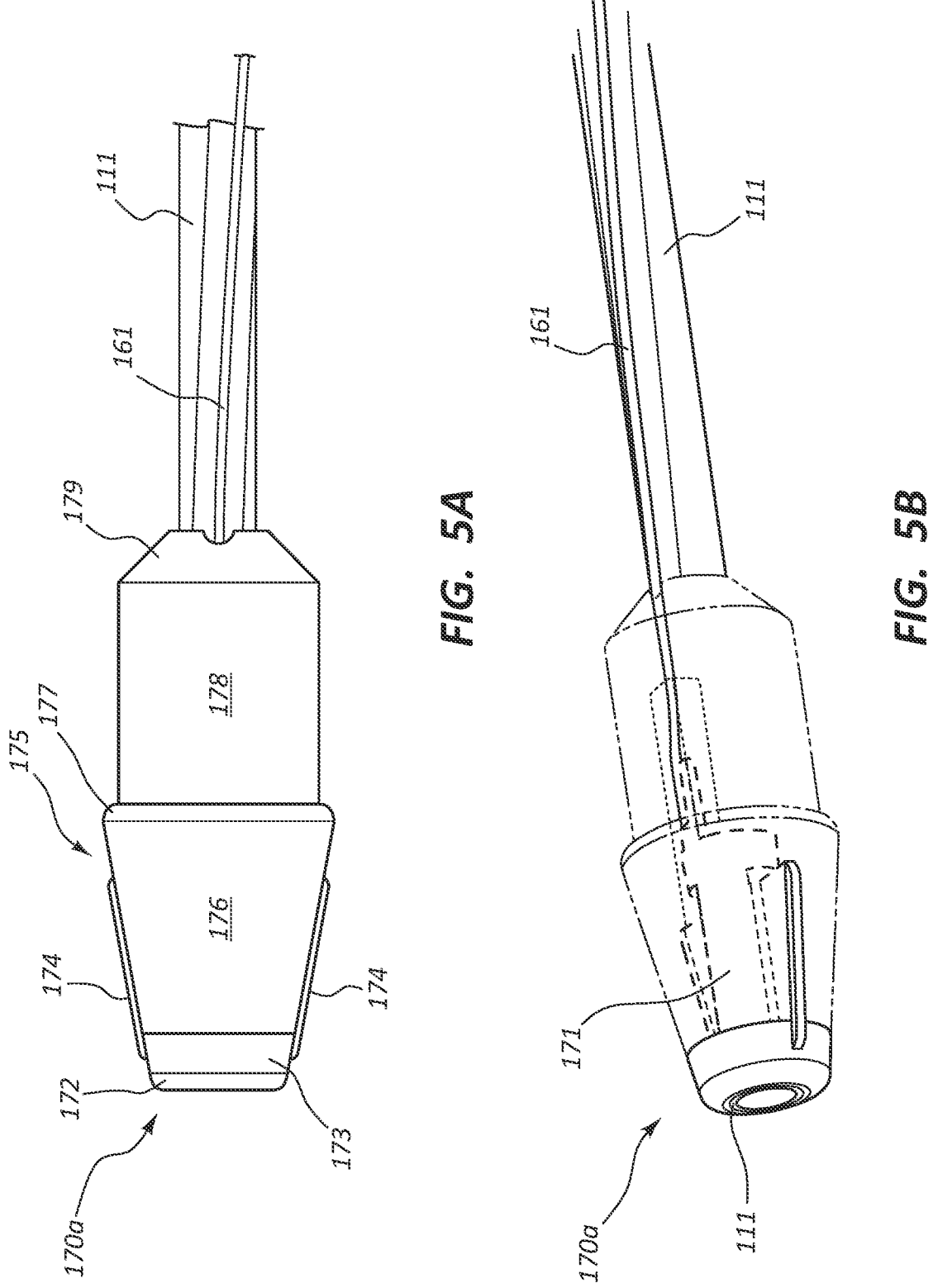
FIG. 5A illustrates a profile view of one embodiment of a tip electrode.
FIG. 5B illustrates a perspective view of the same embodiment of FIG. 5A with one variation of an electrode shank shown in phantom.
Figure 5C:
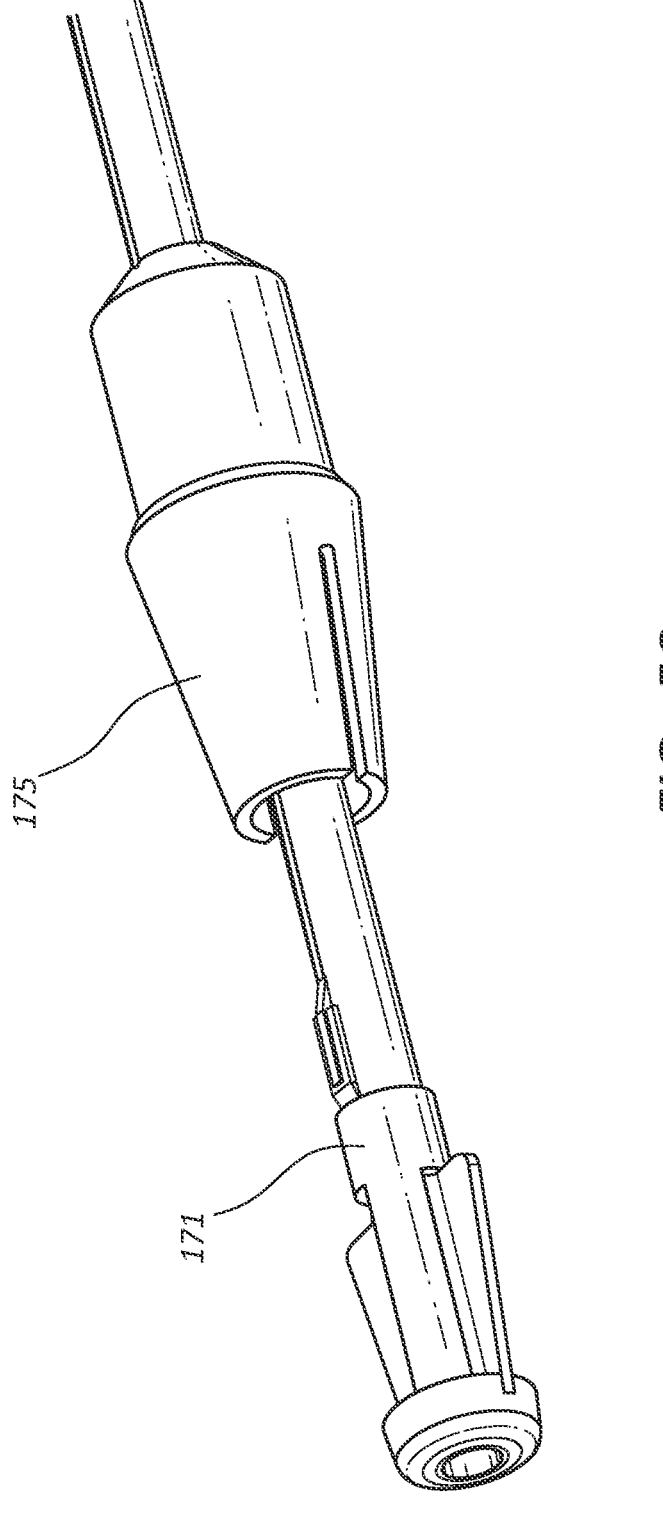
FIG. 5C illustrates the embodiment of FIG. 5B with the housing retracted and the electrode shank visible.

For example, FIG. 5A illustrates a profile view of one embodiment of a tip electrode 170a. The tip electrode 170a comprises a blunt leading edge 172, a collar 173, and two fins 174. These portions of the tip 170a comprise the electrode portion. The tip electrode 170a includes a housing 175. The housing 175 includes a distal taper 176 to minimize physical resistance as the tip electrode 170a is pushed through tissue. The housing 175 includes step 177 that transitions the proximal end of the distal taper 176 to a neck 178. The housing 175 is sized and configured so that an outer sheath 116 (see FIG. 8) of the delivery catheter assembly 110 can butt up against the step 177 and reside over the neck 178, allowing the outer sheath 116 to be flush with the maximum outer diameter of the housing 175. The housing 175 further includes the chamfer 179 that tapers the neck 178 to a guidewire sheath 111 that extends through the tip electrode 170a and is flush with the leading edge 172. The chamfer 179 at the proximal end of the tip electrode 170a reduces the likelihood of the tip electrode 170a catching on tissue or a deployed prosthesis as the tip electrode 170a is withdrawn post-deployment of a prosthesis. FIG. 5B illustrates a perspective view of the same embodiment with an electrode shank 171 shown in phantom and electrically connected via resistance welding to the conductor 161. FIG. 5C illustrates another perspective view with the housing 175 retracted, further illustrating the electrode shank 171. In FIGS. 5B and 5C, the electrode shank 171 comprises an internal hypotube.

The blunt leading edge 172, the collar 173, and the two fins 174 may be made of an electrically-conductive material, such as a metal. A variety of manufacturing techniques may be used. For example, the blunt leading edge 172 may be machined or metal injection molded and the fins 174 and the electrode shank 171 may be stamp manufactured. The fins 174 may not be present or any number of fins may be present, such as one to four fins. Additionally, the fins 174 may vary in length relative to the distal taper 176. The blunt leading edge 172, the collar 173, and the two fins 174 may be coated with an insulative low-friction coating, such as polytetrafluoroethylene (PTFE) or insulative formulations of ElectroBond or VisiBond, to further focus electrical energy and further focus the current density. For example, a uniform PTFE coating could be applied; however, the coating would not coat/adhere to sharp edges, thereby focusing the electrical current at those sharp edges. Alternatively or additionally, a portion of the surface could be masked to prevent coating adhesion. Instead of or in addition to masking, cutting surfaces could be ground or trimmed to removed coating material from the cutting surfaces. Additionally, the cutting surfaces could be coated with a conductive low-friction coating, such as conductive formulations of ElectroBond. The housing 175 may be made of a molded insulator, such as a ceramic. Alternatively, the housing 175 may be made of a conductive material and coated with an insulator.

Figures 6, 7:
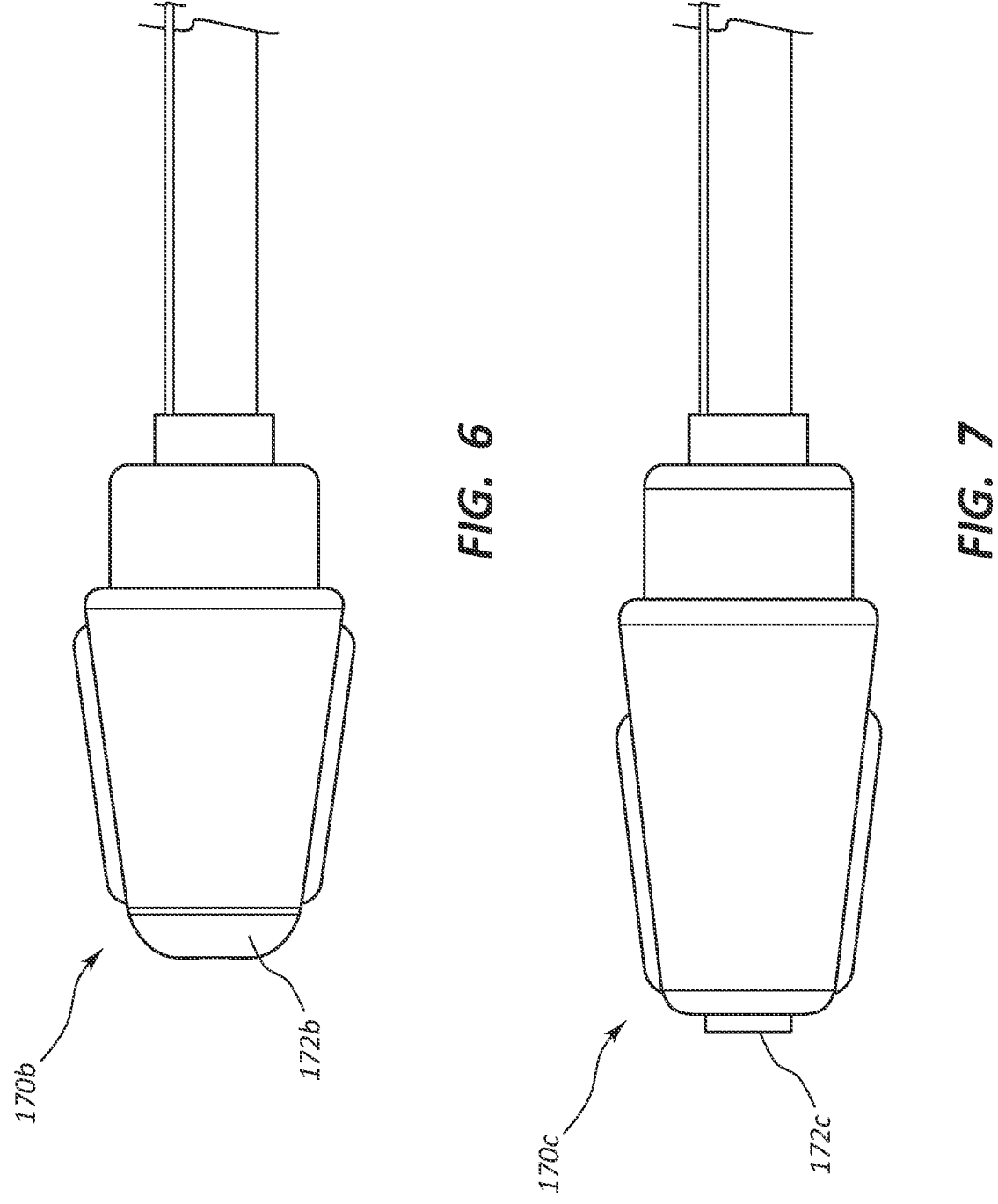
FIG. 6 illustrates a profile view of another embodiment of a tip electrode.
FIG. 7 illustrates a profile view of an additional embodiment of a tip electrode.
Figures 8, 9A:
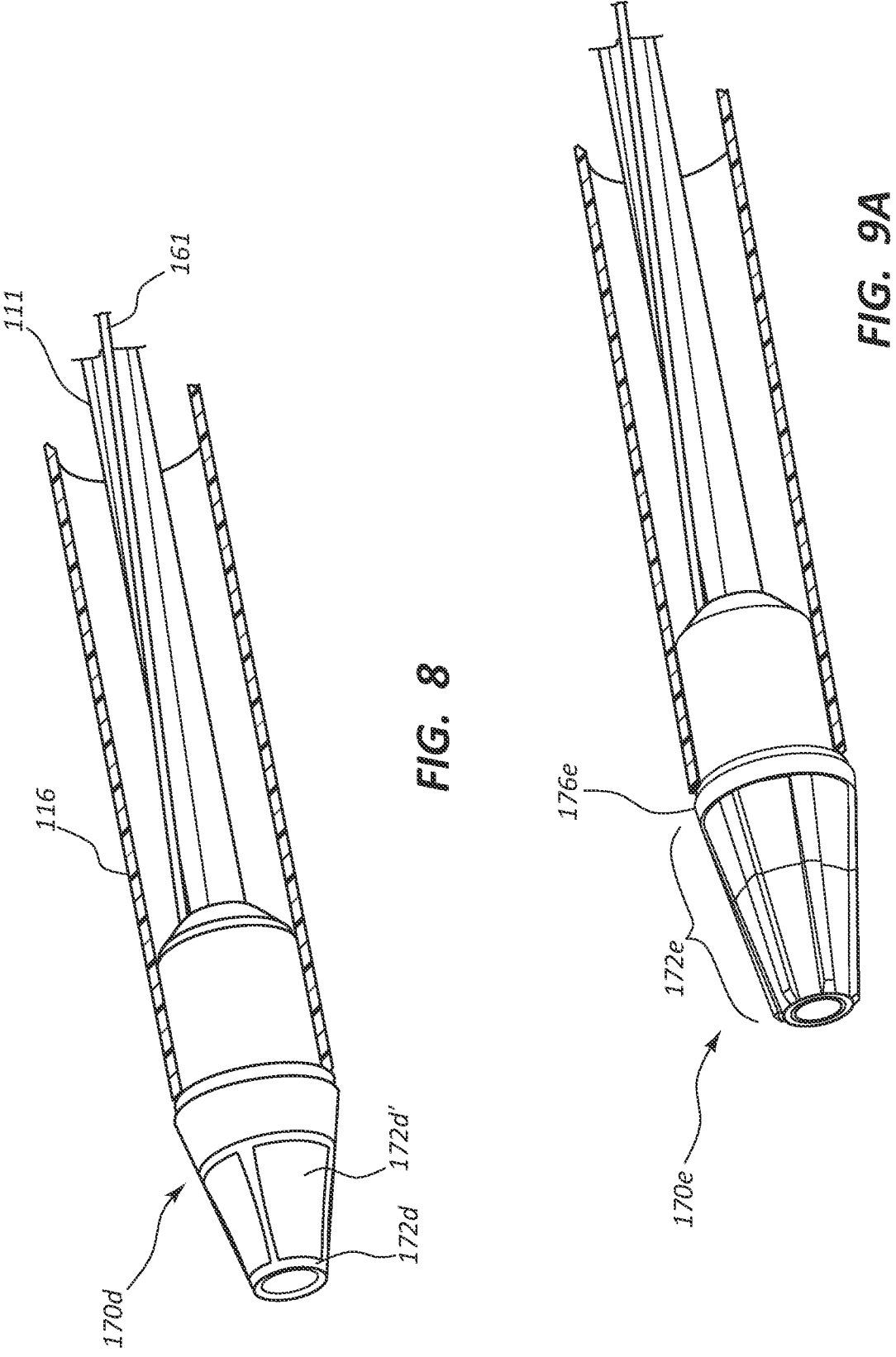
FIG. 8 illustrates a perspective view of another embodiment of a tip electrode.
FIG. 9A illustrates a perspective view of another embodiment of a tip electrode.

One of ordinary skill in the art, with the benefit of this disclosure, would understand that the tip electrode 170 may be designed in a number of different ways. For example, FIG. 6 illustrates a profile view of another embodiment of a tip electrode 170b. The leading edge 172b is less blunt in this embodiment, as compared to the tip electrode 170a. FIG. 7 illustrates a profile view of another embodiment of a tip electrode 170c. In this embodiment, the leading edge 172c is sharp. FIG. 8 illustrates a perspective view of yet another embodiment of a tip electrode 170d. In this embodiment, the leading edge 172d includes PTFE coated regions 172d' that focus the electrical current outside of the PTFE coated regions **172*d'*. FIG. 9A illustrates a perspective view of still yet another embodiment of a tip electrode 170*e*. In this embodiment, the leading edge 172*e* occupies the majority of the distal taper 176*e*. The tip electrode 170*e* may be all metal and coated with an insulator to focus the electrical current to the outer edges of the tip electrode 170*e***.

Figures 9B, 9C:
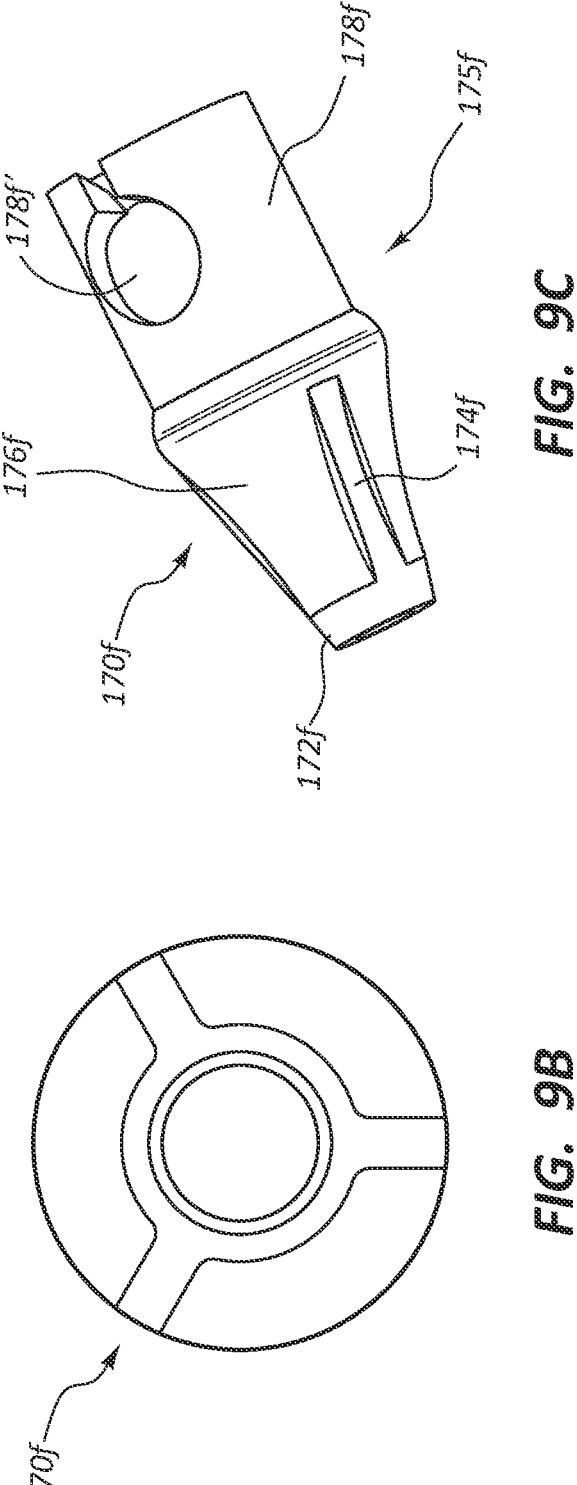
FIG. 9B illustrates a frontal view of another embodiment of a tip electrode.
FIG. 9C illustrates a perspective view of the embodiment of FIG. 9B.

FIGS. 9B and 9C illustrate another embodiment of a tip electrode **170*f*. The tip electrode 170*f* tapers distally towards a leading edge 172*f*. A distal taper 176*f* forms concave regions that define fins 174*f*. Three fins 174*f* are depicted, but 1-3 fins 174*f* may be present. The housing 175*f* may be metal and may be shaped, for example, by machining or metal injection molding. The housing 175*f* may be coated with an insulator, such as PTFE, and the cutting surface either exposed by machining or protected by masking. A neck 178*f* includes a proximal pocket 178*f'* where the conductor 161** may be resistance welded.

Figure 9E:
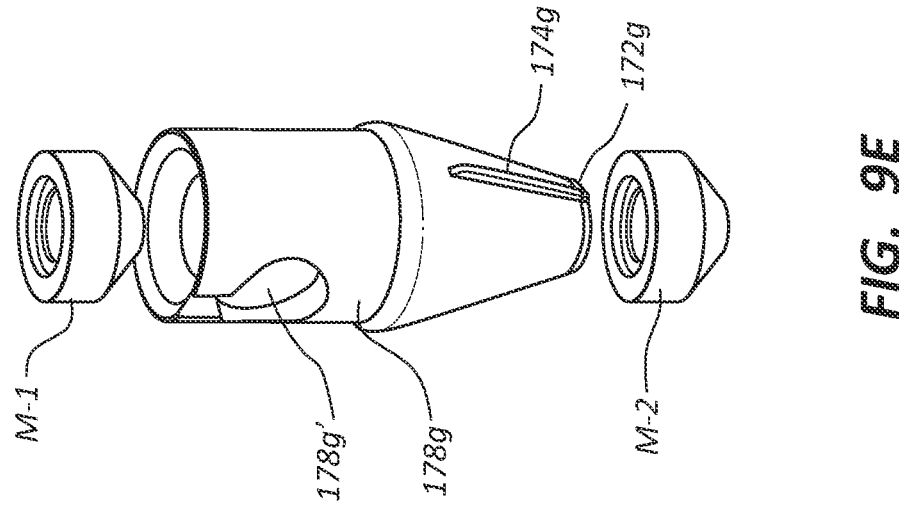
FIG. 9E illustrates masking elements for use with the embodiment of FIG. 9D.
Figure 9D:
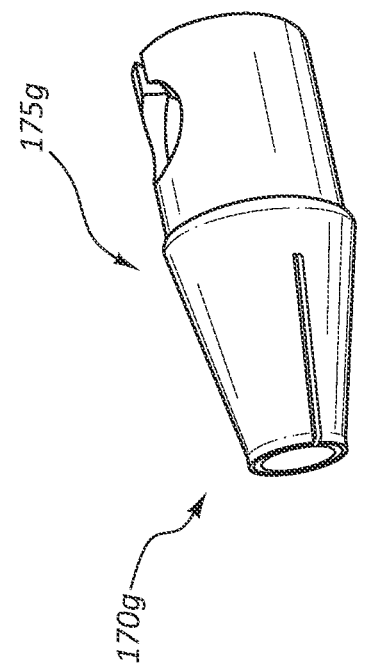
FIG. 9D illustrates a perspective view of another embodiment of a tip electrode.
Figure 9F:
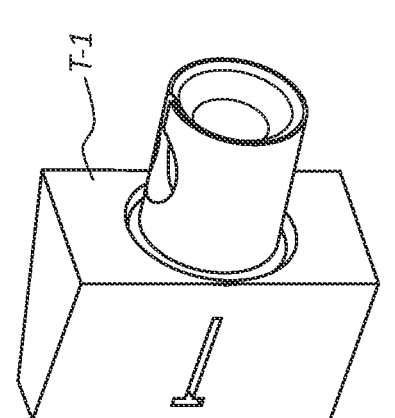
FIG. 9F illustrates a trim device for use with the embodiment of FIGS. 9D and 9E.
Figure 9F:

FIGS. 9D-9F illustrate another embodiment of a tip electrode **170*g* and also a method of making it. A housing 175*f* may be made of metal and shaped by the processes discussed above. A mask M-1 may be inserted in a proximal end of a neck 178*g*. A leading edge 172*g* may be inserted in a mask M-2. The housing 175*g* may then be coated with an insulator, such as PTFE. The masks M-1 and M-2 may then be removed. The housing 175*g* may next be inserted in a trim device T-1 where fins 174*g* are trimmed to expose the outer edges of the fins 174*g*. Two fins 174*g* are depicted; however, 1-3 fins 174*g* may be present. A neck 178*g* includes a proximal pocket 178*g'* where the conductor 161** may be resistance welded.

Figures 9G, 9H:
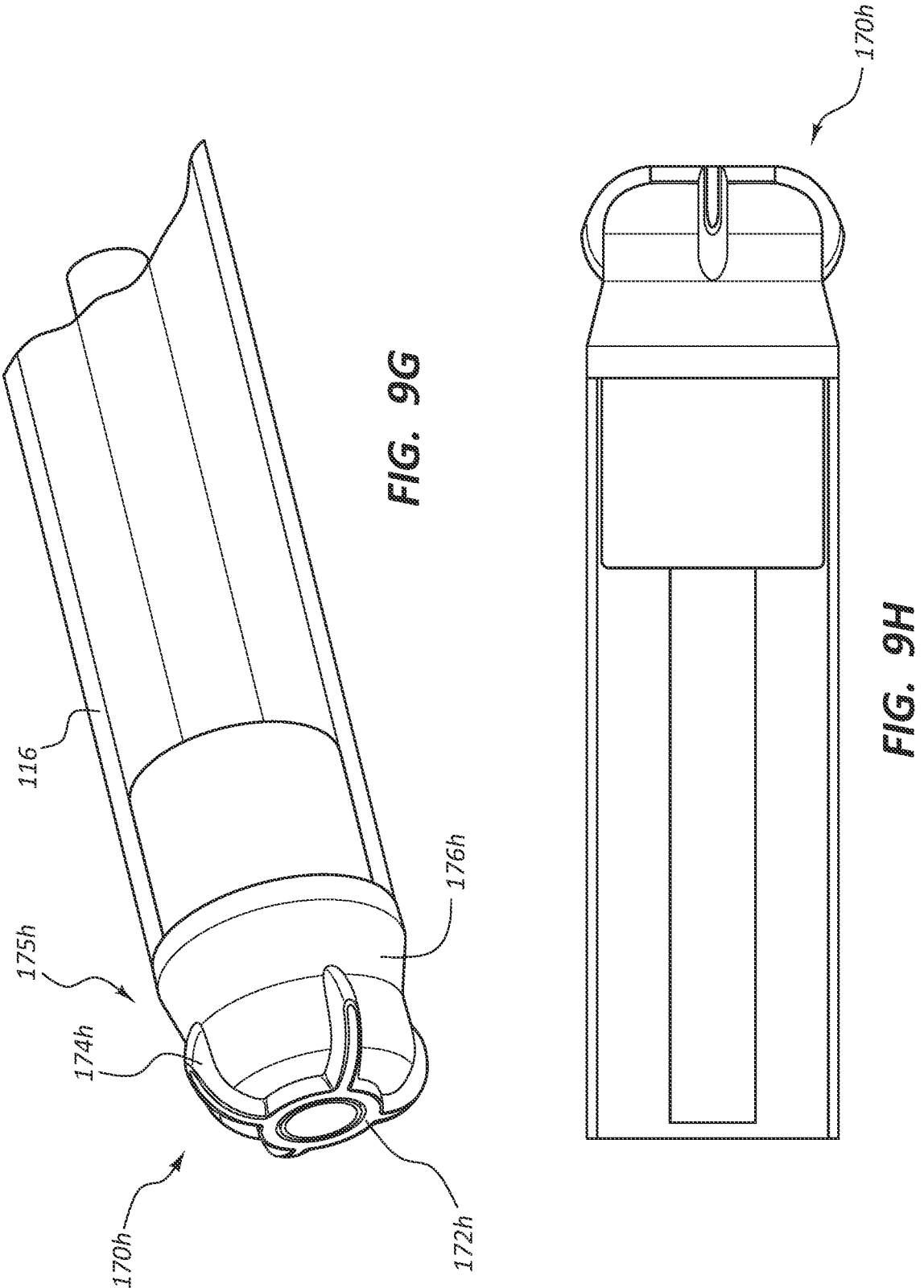
FIG. 9G illustrates a perspective view of another embodiment of a tip electrode.
FIG. 9H illustrates a profile view of the embodiment of FIG. 9G.

FIGS. 9G and 9H illustrate another embodiment of a tip electrode **170*h*. Fins 174*h* are separate from each other and are located distal to a distal taper 176*h*. The fins 174*h* connect to a leading edge 172*h*. The distal taper 176*h* may spread cut tissue equal to the diameter of the outer sheath 116. A housing 175*h* may be made of metal and shaped by the processes discussed above. The housing 175*h* may be coated with an insulator, such as PTFE, and the cutting surfaces either exposed by machining or protected by masking. Four fins 174*h* are depicted; however, 1-4 fins 174*h* may be present. A proximal pocket (not shown) may be present where the conductor 161** may be resistance welded.

Figure 9I:
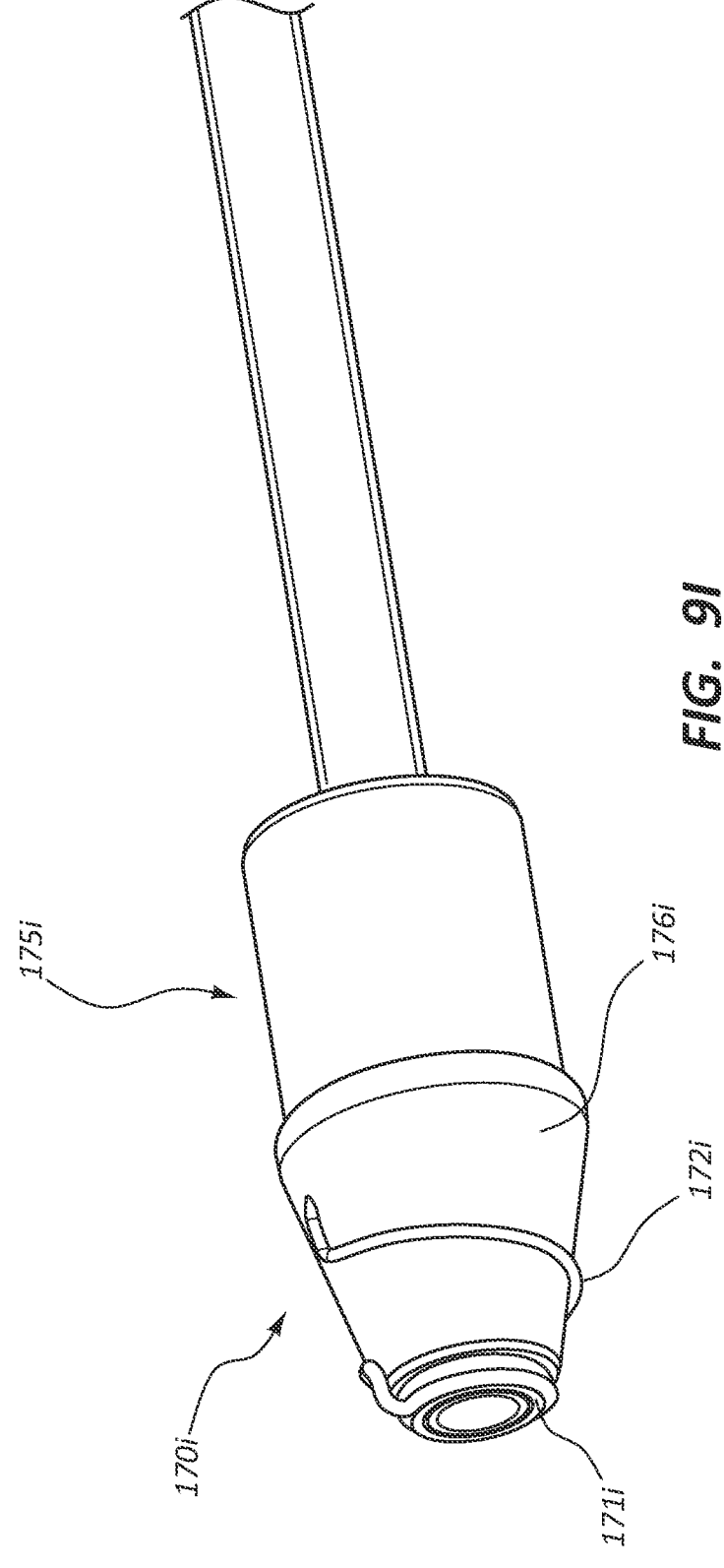
FIG. 9I illustrates another embodiment of a tip electrode.

FIG. 9I illustrates yet another embodiment of a tip electrode **170*i*. A housing 175*i* may be made of a molded ceramic. An internal metal hypotube 171*i* is present inside the housing 175*i* and extends distally beyond the housing 175*i*. The conductor 161 (not shown) may be resistance welded to the metal hypotube 171*i*. A resistive wire 172*i* is wrapped twice around the exposed portion of the metal hypotube 171 and then helically wraps around a distal taper 176*i* of the housing 175*i*. The resistive wire 176*i* may have a variety of diameters, such as, about 0.0004 inch to about 0.0008 inch. The resistive wire 172*i* functions as the cutting surface for the tip electrode 170*i***.

Figures 9J, 9K:
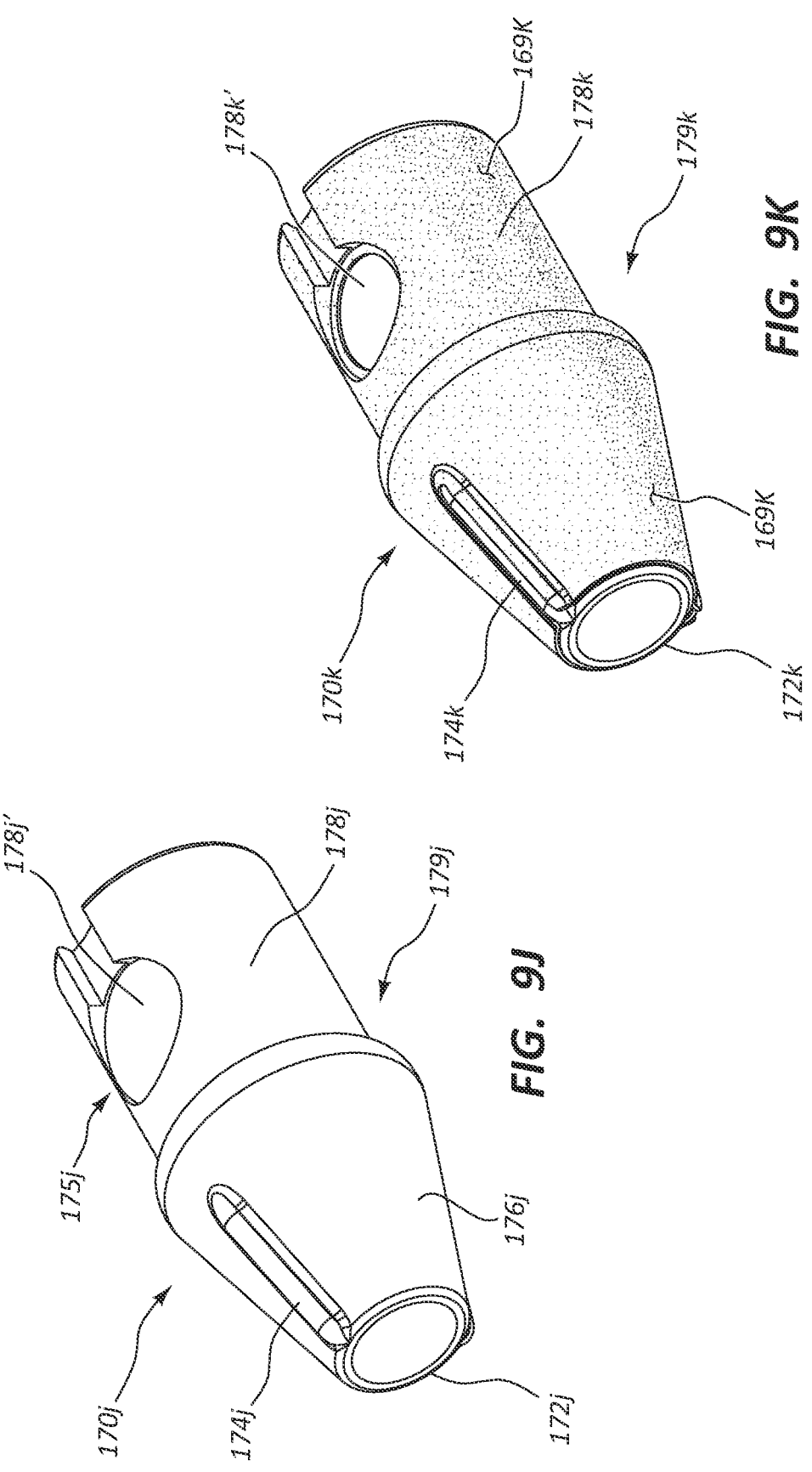
FIG. 9J illustrates a perspective view of another embodiment of a tip electrode.
FIG. 9K illustrates a perspective view of the tip electrode of FIG. 9J with a coating.

FIGS. 9J and 9K illustrate another embodiment of a tip electrode **170*j*. The tip electrode 170*j* has a housing 175*j* that may include a tapered portion 176*j* that tapers distally towards a leading edge 172*j* and a neck portion 178*j*. The tapered portion 176*j* may have a conic shape. The tapered portion 176*j* may include a plurality of fins 174*j* that project radially outward from the tapered portion 176*j*. Two fins 174*j* are depicted, however, embodiments with additional fins are within the scope of this disclosure. The housing 175*j* may be fabricated from metal and may be shaped, for example, by machining or metal injection molding. The neck 178*j* may include a proximal pocket 178*j'* where the conductor 161** may be resistance welded.

FIG. 9K further illustrates the tip electrode **170*k* with a coating 169*k*. The coating 169*k* may be a dielectric coating, such as ElectroBond or VisiBond. The internal surfaces of the tip electrode 170*k* may be masked during coating to facilitate adhesive bonding. The coating may be configured to only coat certain portions of the tip electrode 170*k* or the tip electrode 170*k* may be wholly coated and then laser ablated to remove the coating from certain portions of the tip electrode 170*k*. For example, the leading edge 172*k*, the top surface of the fins 174*k*, and the proximal pocket 178*k'*** may be uncoated.

It should be understood that the tip electrodes **170*a*-170*k* are exemplary and do not limit the scope of this disclosure. For example, fins, if present, may extend to the distal end of the leading edge. The leading edge may be blunt or sharp. Additionally, the various features of the tip electrodes 170*a*-170*k*** may be combined together in ways not illustrated or specifically discussed herein.

Figure 10B:
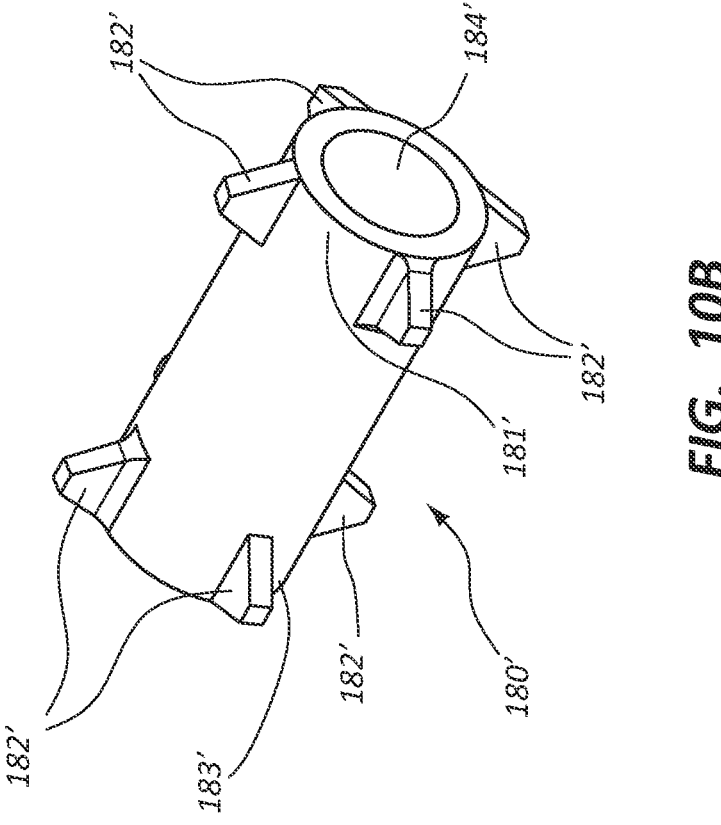
FIG. 10B illustrates a perspective view of another embodiment of a prosthesis anchor.
Figure 10A:
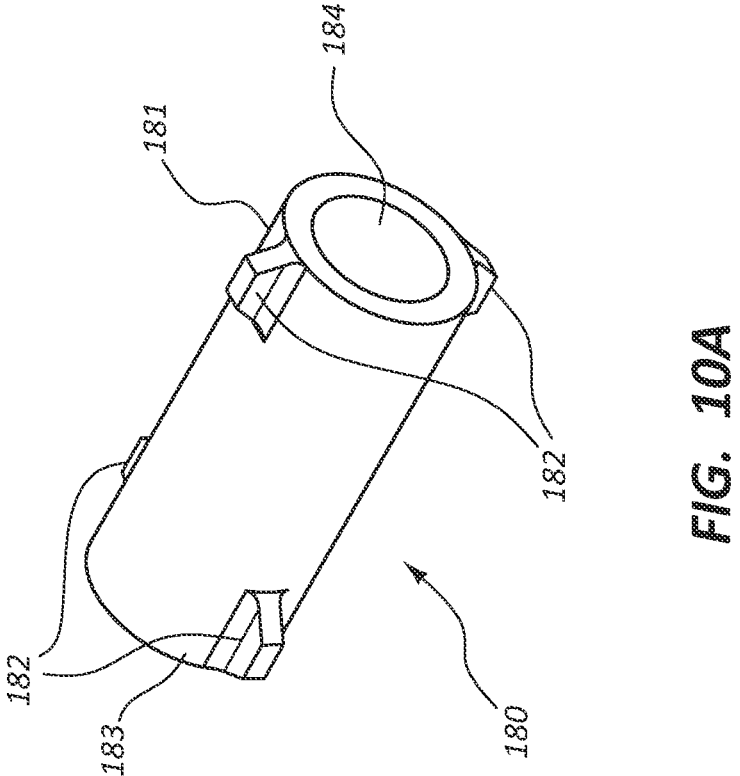
FIG. 10A illustrates a perspective view of a prosthesis anchor.

FIG. 10A illustrates a first embodiment of a prosthesis anchor 180 and FIG. 10B illustrates another embodiment of a prosthesis anchor 180'. The prosthesis anchor 180 of FIG. 10A comprises a cylindrical shape and an internal lumen 184. The internal lumen 184 of the prosthesis anchor 180 is configured to be disposed around the guidewire sheath 111. The prosthesis anchor 180 may further include a plurality of protuberances 182 that extend radially from the cylinder. The protuberances 182 are configured to interact with the prosthesis (200 of FIG. 11B) and secure the prosthesis (200 of FIG. 11B) within a prosthesis pod (117 of FIGS. 11 and 11B) as discussed below. The protuberances 182 may have a radial height that range from 0.005 to 0.025 inches. The protuberances 182 may be disposed adjacent a distal end 181 of the prosthesis anchor 180 and/or adjacent a proximal end 183 of the prosthesis anchor 183. Protuberances 182 along other points of the prosthesis anchor 180 are likewise within the scope of this disclosure. In the embodiments of FIG. 10B, the protuberances 182' on the distal end 181' are aligned with the protuberances 182' on the proximal end 183' of the prosthesis anchor 180'. In other embodiments, such as the embodiment of FIG. 10A, the protuberances 182 on the distal end 181 may be misaligned with the protuberances 182 on the proximal end 183. In some embodiments, the protuberances 182 on each end of the prosthesis anchor 180 may be spaced equally around the circumference of the cylinder.

In some embodiments, as illustrated in FIG. 10A, there may be four protuberances 182, with two protuberances 182 on the distal end 181 and two protuberances 182 on the proximal end 183. In some embodiments, such as shown in FIGS. 10B, there may be eight protuberances 182', with four protuberances 182' on the distal end 181' and four protuberances 182' on the proximal end 183'. Embodiments wherein the prosthesis anchor 180 has more or less than four or eight protuberances are also within the scope of this disclosure.

As discussed previously, the guidewire sheath 111 extends to the distal end of the tip electrode 170. The guidewire sheath 111 extends the entire length of the delivery catheter assembly 110 and the housing assembly 130. In the illustrated embodiments, the housing assembly 130 includes a female luer lock adapter 138 configured for allowing access to the lumen defined by the guidewire sheath 111 (see, e.g., FIG. 2B). Referring to area 10 of FIG. 1 and corresponding FIGS. 10 and 10A, a mid-sheath 112 circumscribes a proximal region **111*a* of the guidewire sheath 111. The prosthesis pod 117 circumscribes a portion of a distal region 111*b* of the guidewire sheath 111. The prosthesis pod 117 is configured to receive a prosthesis 200 (in elongated and stretched form). The outer sheath 116 circumscribes the mid-sheath 112 and circumscribes the prosthesis pod 117. The outer sheath 116 is translatable over the mid-sheath 112 and the prosthesis pod 117 so as to allow deployment of the prosthesis 200**, as is discussed in more detail later.

Figures 11, 11A, 11B:
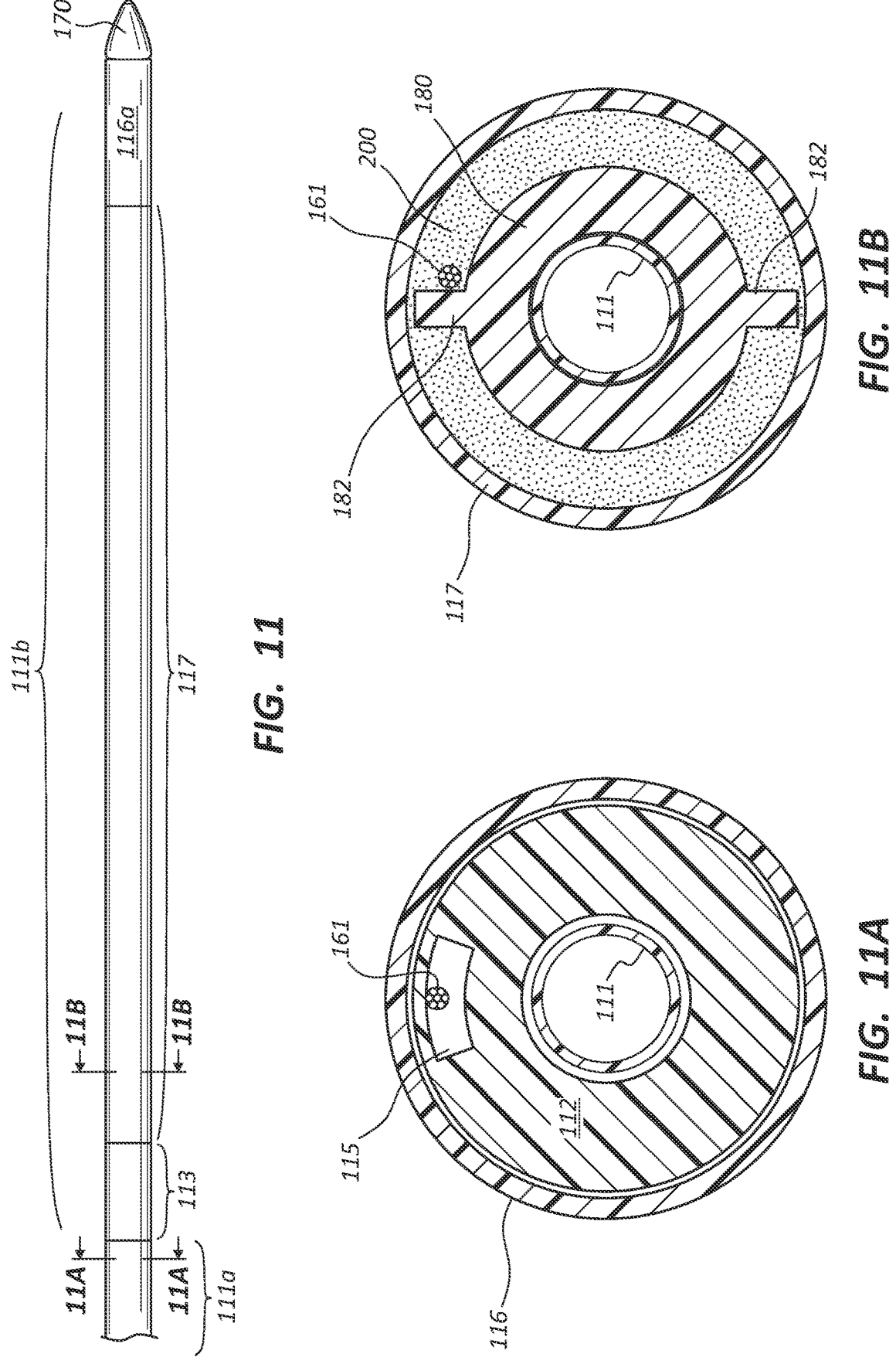
FIG. 11 illustrates an enlarged view of the area 10 of FIG. 1.
FIG. 11A illustrates a cross-sectional view taken along the line 11A of FIG. 11.
FIG. 11B illustrates a cross-sectional view taken along the line 11B of FIG. 11.

FIG. 11A illustrates a cross-sectional view taken along the line 11A of FIG. 11. In this embodiment, the mid-sheath 112 includes a second lumen 115 configured to provide access for the conductor 161. The mid-sheath 112 may be extruded and include a number of lumens for different uses. In some embodiments, the conductor 161 may be embedded within the mid-sheath 112.

FIG. 11B illustrates a cross-sectional view taken along the line 11B of FIG. 11. This embodiment illustrates a cross-sectional view of the prosthesis pod 117 taken along the protrusions 182 on a proximal end 183 of a prosthesis anchor 180. The prosthesis anchor 180 of this embodiment is disposed adjacent a proximal end of the prosthesis pod 117, the prosthesis anchor being disposed around the guidewire lumen 111 and within the outer sheath 116. The prosthesis anchor 180 (positioned on the guidewire lumen 111) is thus disposed within the prosthesis 200 when the prosthesis 200 is constrained within the prosthesis pod 117. The protuberances 182 interact and secure the prosthesis 200 in place during deployment of the prosthesis 200. In some embodiments, the prosthesis 200 includes a cover coupled to the braided or woven wires of the prosthesis 200 and the protuberances 182 may interact directly with the cover. For example, when the prosthesis 200 is crimped and constrained within the prosthesis pod 117, portions of the cover disposed between cells of the prosthesis 200 may bulge outward and inward giving the crimped prosthesis 200 an uneven or bumpy inner and outer texture. The prosthesis anchor 180 may interact with this texture and surface to secure the prosthesis 200 with respect to the prosthesis anchor 180 and thus with respect to the guidewire lumen 111. In some embodiments, the conductor 161 may be disposed between the prosthesis anchor 180 and the prosthesis 200 along this portion of the prosthesis pod 117.

Figure 12:
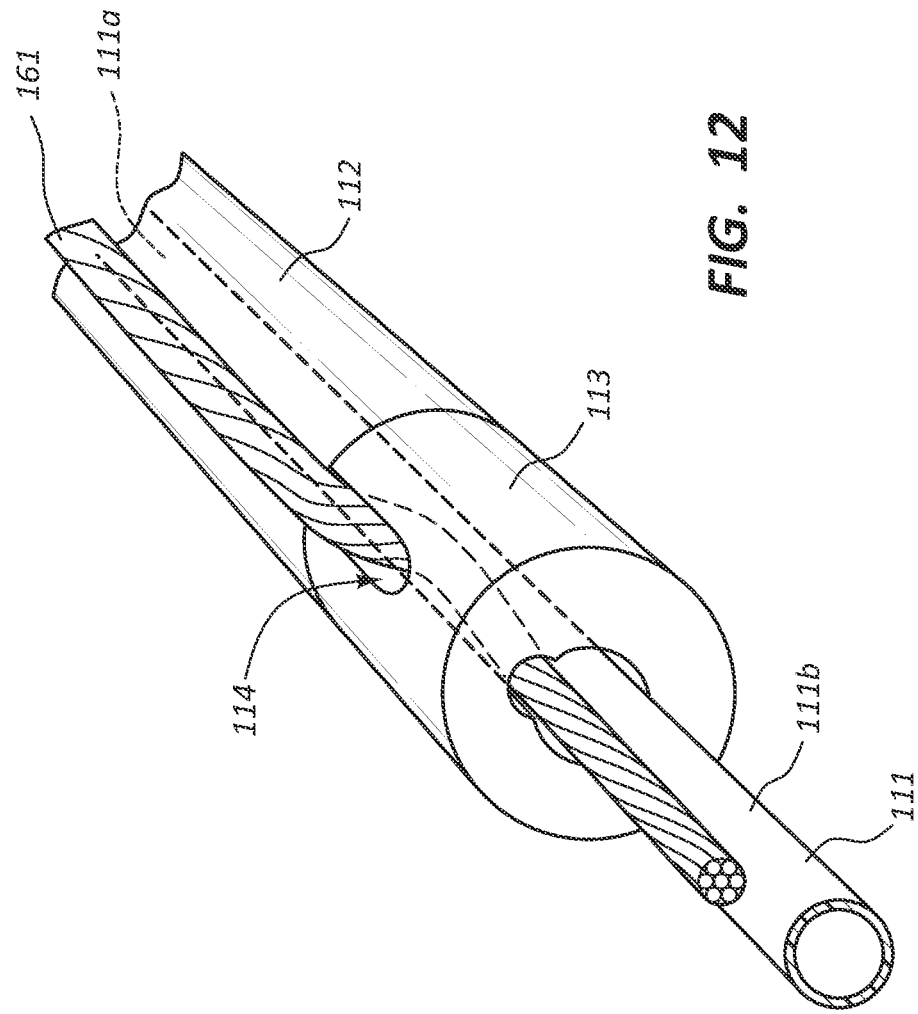
FIG. 12 illustrates one embodiment of a proximal marker.

FIG. 12 illustrates an alternative embodiment where the single conductor 161 extends between the outer sheath 116 and the mid-sheath 112 along the proximal region 111*a* of the guidewire sheath 111 and then extends on an outer surface of the guidewire sheath 111 along the distal region 111*b* of the guidewire sheath 111. FIG. 12 further illustrates a proximal marker 113 in-line with the mid-sheath 112 and located between a distal end of the mid-sheath 112 and a proximal end of the prosthesis pod 117. The proximal marker 113 comprises a crossover channel 114 between the outer surface of the proximal marker 113 and a distal surface of the proximal marker 113. The conductor 161 transitions via the crossover channel 114 from between the outer sheath 116 and the mid-sheath 112 to the outer surface of the guidewire sheath 111. The proximal marker 113 may be modified to mate with the second lumen 115 when such an embodiment is used. The proximal marker 113 may be configured to provide endoscopic and/or fluoroscopic visibility to a user.

With reference to FIG. 8, in some embodiments, the conductor 161 may be helically wrapped around the outside diameter of the guidewire sheath 111. In some instances, one or more helical loops around the guidewire sheath 111 by the conductor 161 may provide compliance, allowing the assembly to flex around bends (such as when advanced within the body) without straining the conductor 161 by pulling it tight when the assembly is in a bent or curved profile. In some instances the conductor 161 may comprise a litz wire. In other instances, the conductor 161 may comprise a single filament flat wire, such as, for example, a 0.003 inch by 0.014 inch or a 0.0024 inch by 0.017 inch. A flat wire may be easier to resistance weld. The flat wire may be coated or uncoated. In some embodiments, the conductor 161 may comprise a round coated metal wire, for example, copper. The wire may be laser ablated for ease of resistance welding. In some embodiments, the conductor 161 may include a wire braid that helps increase kink resistance.

Referring back to FIG. 4, in this embodiment, the conductor 161 is shown adjacent the guidewire sheath 111. In contrast, in the embodiments illustrated in FIGS. 10A and 11, the conductor 161 is separated from the guidewire sheath 111 by all or much of the thickness of the mid-sheath 112. This may reduce capacitive coupling.

The guidewire sheath 111, the mid-sheath 112 (and proximal marker 113), and the outer sheath 116 may be made of a variety of materials. For example, the guidewire sheath 111 may have a three-layer construction with a PTFE-polyimide blend as the inner layer to provide reduced friction with a guidewire, a polyimide middle layer to provide strength without bulk, and a polyether block amide, such as Pebax, outer layer to promote adhesion to the electrode tip 170 and any over-molded features. In some embodiments, the guidewire sheath 111 may not include metallic braiding, so as to minimize capacitive coupling with the conductor 161; however, in other embodiments, metallic braiding may be present. The mid-sheath 112 may comprise PTFE, given its high dielectric strength, so as to minimize capacitive coupling between the conductor 161 and the guidewire sheath 111 (when the mid-sheath 112 is placed between the two). Other options include a polyether block amide or nylon. Additionally, the materials of the mid-sheath 112 could have different durometers in different regions to achieve flex-zones in the delivery catheter assembly 110. The outer sheath 116 may have a hydrophilic coating to increase lubricity of the delivery catheter assembly 110. The outer sheath 116 may include PTFE as an inner layer to reduce friction and may include para-aramid fiber braid or axially-oriented fibers to reduce stretching of the delivery assembly 110. The outer sheath 116 may also include materials with different durometers, such as to achieve softer flex-zones. The mid-sheath 112 and the outer sheath 116 may also not include metallic braiding, so as to minimize capacitive coupling.

In some embodiments, the guidewire lumen 111, the mid-sheath 112, and the outer sheath 116 may be encompassed within the housing assembly 130 by a hypotube or a pair of hypotubes. In some embodiments, the hypotube may be fabricated from stainless steel. In some embodiments, an internal hypotube may be fabricated from stainless steel and an outer hypotube may be fabricated from a non-conductive polymer to help improve the dielectric properties. The outer hypotube may be fabricated from polyether ether ketone (PEEK) or another suitable material. In some embodiments, the stainless steel hypotube may have a polyethylene terephthalate (PET) or PTFE heat shrink to help improve dielectric properties.

The proximal marker 113 may be green to provide enhanced endoscopic visibility to the user. The distal portion of the outer sheath 116 may be transparent other than a distal marker 116*a* that may be green (such as via a reflow process) for endoscopic visibility. The transparent distal portion can allow for visibility of the proximal marker 113 and the prosthesis pod 117. Metal marker bands may be swaged into or onto the guidewire sheath 111 underneath the proximal marker 113 and the distal marker 116a (relative to when the outer sheath 116 is fully distally extended, prior to deployment of the prosthesis 200) to provide fluoroscopic visibility.

Figures 13, 13A, 14, 14A:
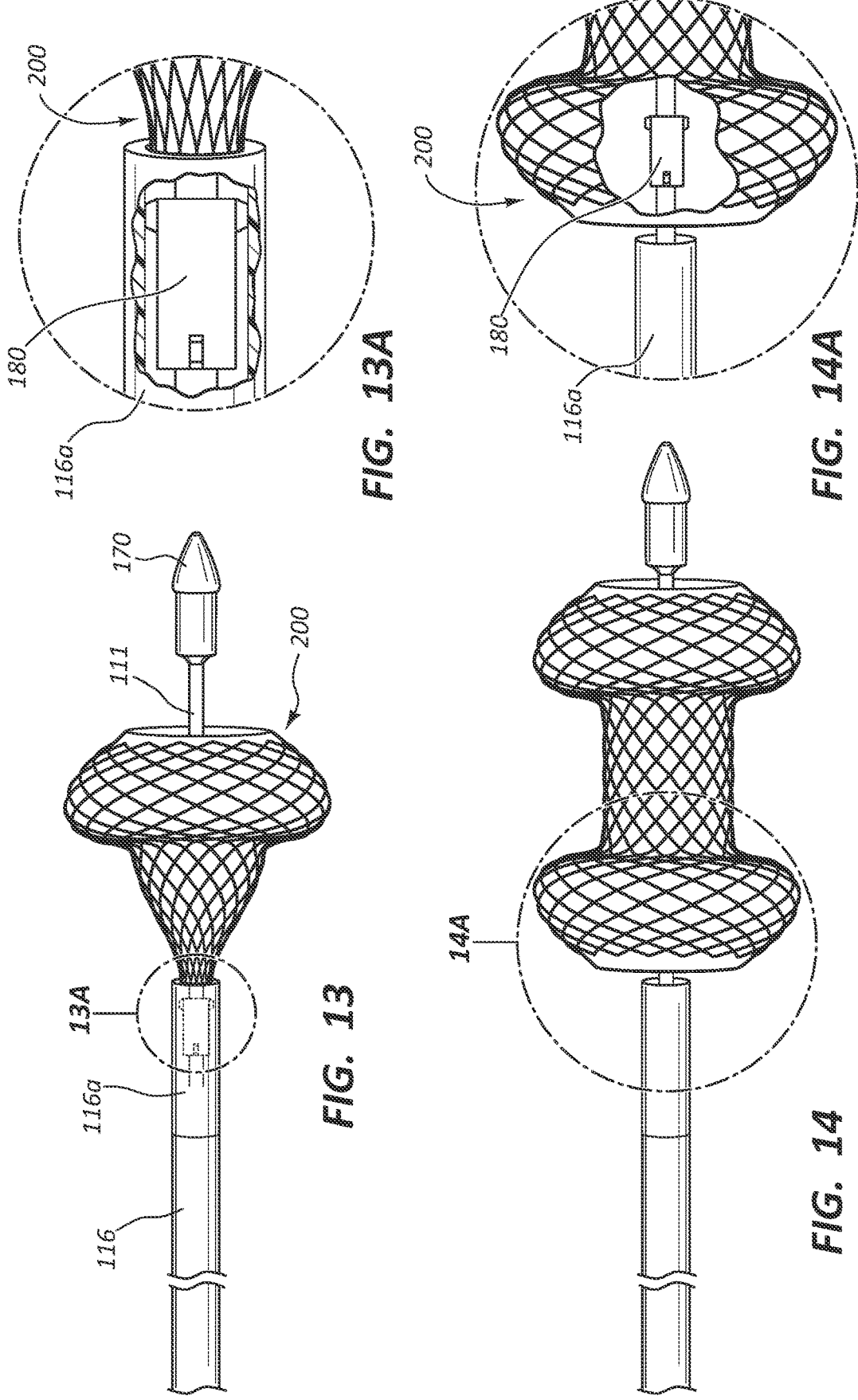
FIG. 13 illustrates one embodiment of partial retraction of an outer sheath and the resulting partial deployment of an exemplary prosthesis.
FIG. 13A illustrates a detailed breakaway view of FIG. 13 of the partial retraction of the outer sheath and the resulting partial deployment of the exemplary prosthesis.
FIG. 14 illustrates one embodiment of full retraction of the outer sheath of FIG. 13 and the resulting full deployment of the exemplary prosthesis.
FIG. 14A illustrates a detailed breakaway view of FIG. 14 of the full retraction of the outer sheath and the resulting full deployment of the exemplary prosthesis.

In use, as the outer sheath 116 is proximally retracted, the distal marker 116a withdraws from the electrode tip 170. As illustrated in FIG. 13, as the outer sheath 116 is retracted about halfway, then the distal half of the prosthesis 200 deploys, illustrated as a stent with flared ends. FIG. 13A illustrates a detailed breakaway view of the prosthesis 200 being partially deployed and the prosthesis anchor 180 securing the prosthesis 200 within the prosthesis pod 117 during deployment. In some embodiments, the prosthesis anchor 180 may be disposed along the flared end portion of the prosthesis 200.

As illustrated in FIG. 14, as the outer sheath 116 is fully retracted, then the proximal half of the prosthesis 200 deploys. The proximal marker 113 provides endoscopic and fluoroscopic visibility (when fluoroscopy is used in addition to or instead of EUS) for the proximal end of the prosthesis pod 117. The distal marker 116a provides endoscopic visibility for the location of the tip electrode 170 and the distal end of the prosthesis pod 117. As the outer sheath 116 is proximally retracted, the distal marker 116a approaches the proximal marker 113. A user can endoscopically see the reduction in distance between the distal marker 116a and the proximal marker 113, thereby providing visual confirmation that the outer sheath 116 is retracting properly. FIG. 14A illustrates a detailed breakaway view of the fully deployed prosthesis 200 with the prosthesis anchor 180 no longer secured to the prosthesis 200.

The delivery assembly 110 may include additional features that are not illustrated in the figures. The prosthesis anchor 180 may comprise a pliant, rigid, and/or heat-shrinkable member that grips the prosthesis 200 and prevents longitudinal displacement.

Referring back to FIGS. 1-3B and 14, the housing assembly 130 includes a first safety tab 141 and a second safety tab 142. The first safety tab 141 prevents deployment of the distal portion of the prosthesis 200 by the handle assembly 150. The second safety tab 142 prevents deployment of the proximal portion of the prosthesis 200 by the handle assembly 150. Exemplary operation of the handle assembly 150 is now described.

FIG. 15 illustrates an exploded view of the housing assembly 130. The handle assembly 150 includes an actuator 151, a track 152, and a sheath adapter 153. The actuator 151 is configured to pivot on portions of the housings 140a and 140b, when assembled. Spring 145 engages with the housings 140a and 140b and is compressed when the actuator 151 is depressed into the housings 140a and 140b. The spring 145 returns the actuator 151 to its unpivoted position when the actuator 151 is no longer depressed by a user. As the actuator 151 is depressed and pivots, it engages with the track 152 and moves the track 152 proximally (unless the first and second safety tabs 141 and 142 are present, as is discussed below). The track 152 is engaged with the sheath adapter 153. As the track 152 proximally retracts, the sheath adapter 153 is brought with it. The sheath adapter 153 is fixedly coupled to the outer sheath 116. Proximal movement of the sheath adapter 153 brings the outer sheath 116 with it. Partial retraction of the sheath adapter 153 results in deployment of the distal half of the prosthesis 200 (see FIG. 13). Complete retraction of the sheath adapter 153 results in full deployment of the prosthesis 200 (see FIG. 14).

Figure 16:
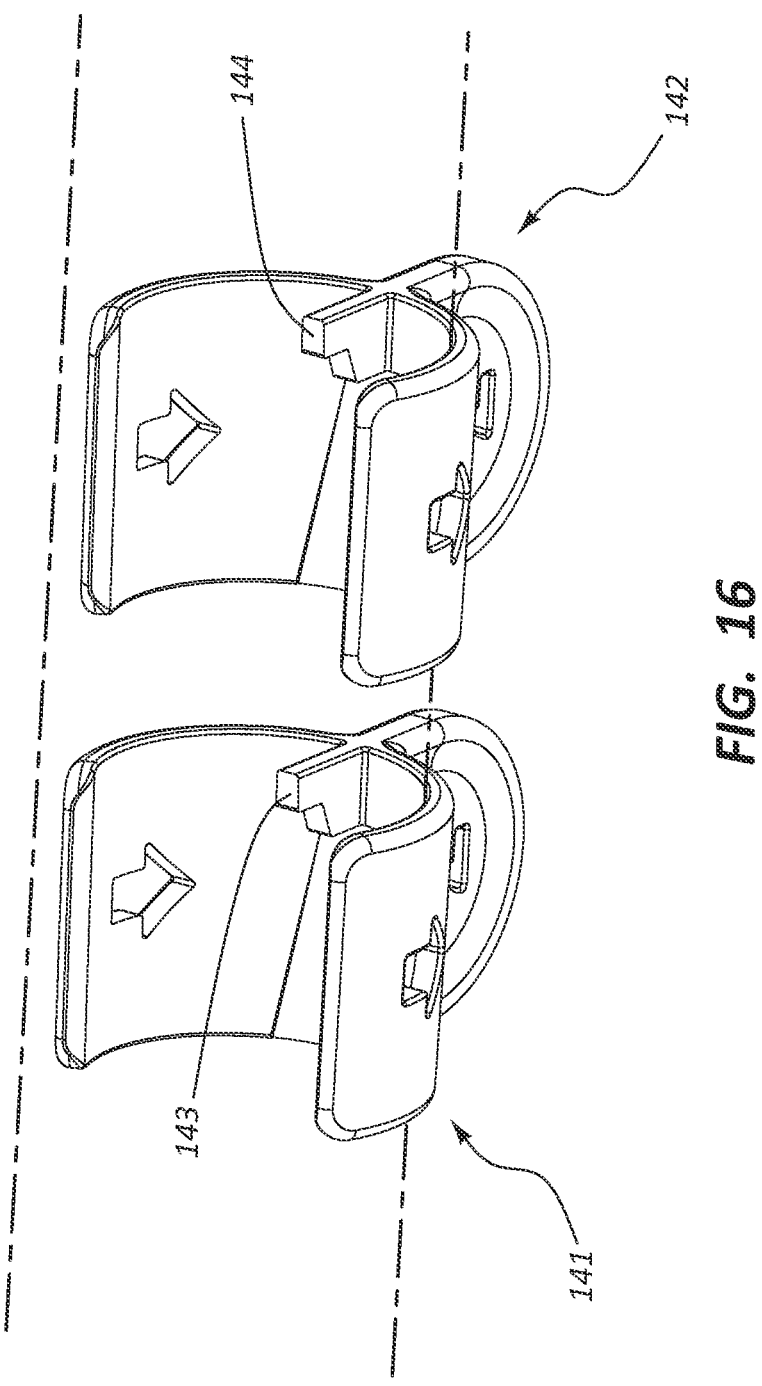
FIG. 16 illustrates a perspective view of the safety tabs of FIG. 1.

The first and second safety tabs 141 and 142 each include a prong 143 and 144, respectively (see FIG. 16), configured to protrude into corresponding holes in the track 152. When the first safety tab 141 is in place, the track 152 is unable to move proximally as the actuator 151 is depressed. With the first safety tab 141 removed, the track 152 is able to proximally retract until the sheath adapter 153 engages with the prong 144 of the second safety tab 142 (which corresponds to deployment of the distal half of the prosthesis 200). Once the second safety tab 142 is removed, the sheath adapter 153 is able to fully proximally retract (which corresponds to full deployment of the prosthesis 200).

Figure 17:
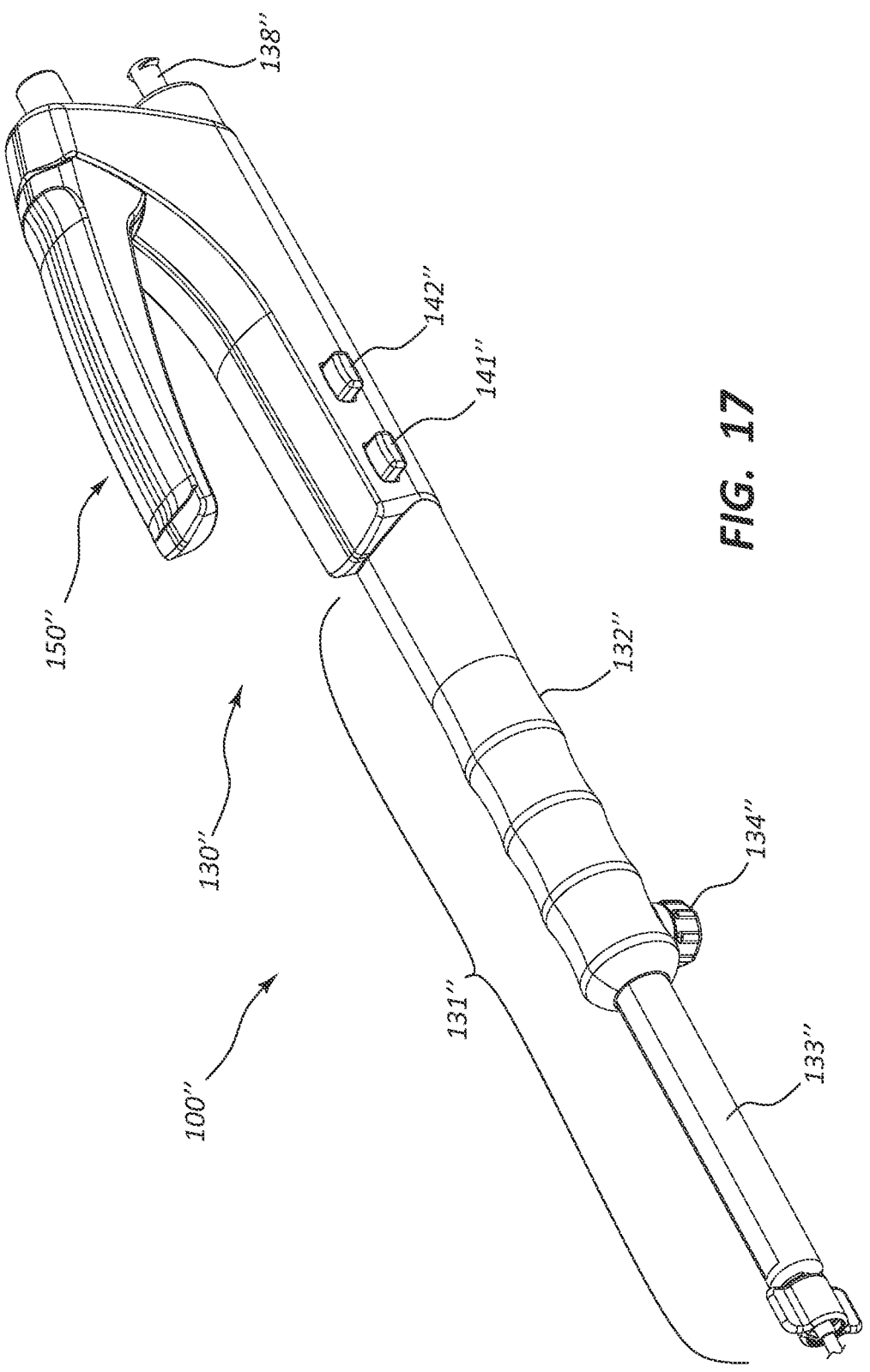
FIG. 17 illustrates a close-up perspective view of another embodiment of a prosthesis delivery device.

FIG. 17 illustrates another embodiment of a prosthesis delivery device 100". The prosthesis delivery device 100" includes an elongate delivery catheter assembly configured for electrosurgery and also configured to retain and deploy a prosthesis. The prosthesis delivery device 100" includes a housing 130" operably coupled to the delivery catheter assembly and configured to connect to an electrosurgical power generator (not shown). The housing assembly 130" may include a handle assembly 150" configured to displace a portion of the delivery catheter assembly to deploy the prosthesis, upon actuation of the handle assembly 150". Similar to the embodiments illustrated in FIGS. 1-4, the prosthesis delivery device 100" may include a slide assembly 131", a slide handle 132", a piston 133", thumbscrew 134", and a female luer lock adapter 138" that may function similar to corresponding components described previously. Prosthesis delivery device 100" may further include a first safety button 141" and a second safety button 142".

Figures 17A, 17B, 17C, 17D:
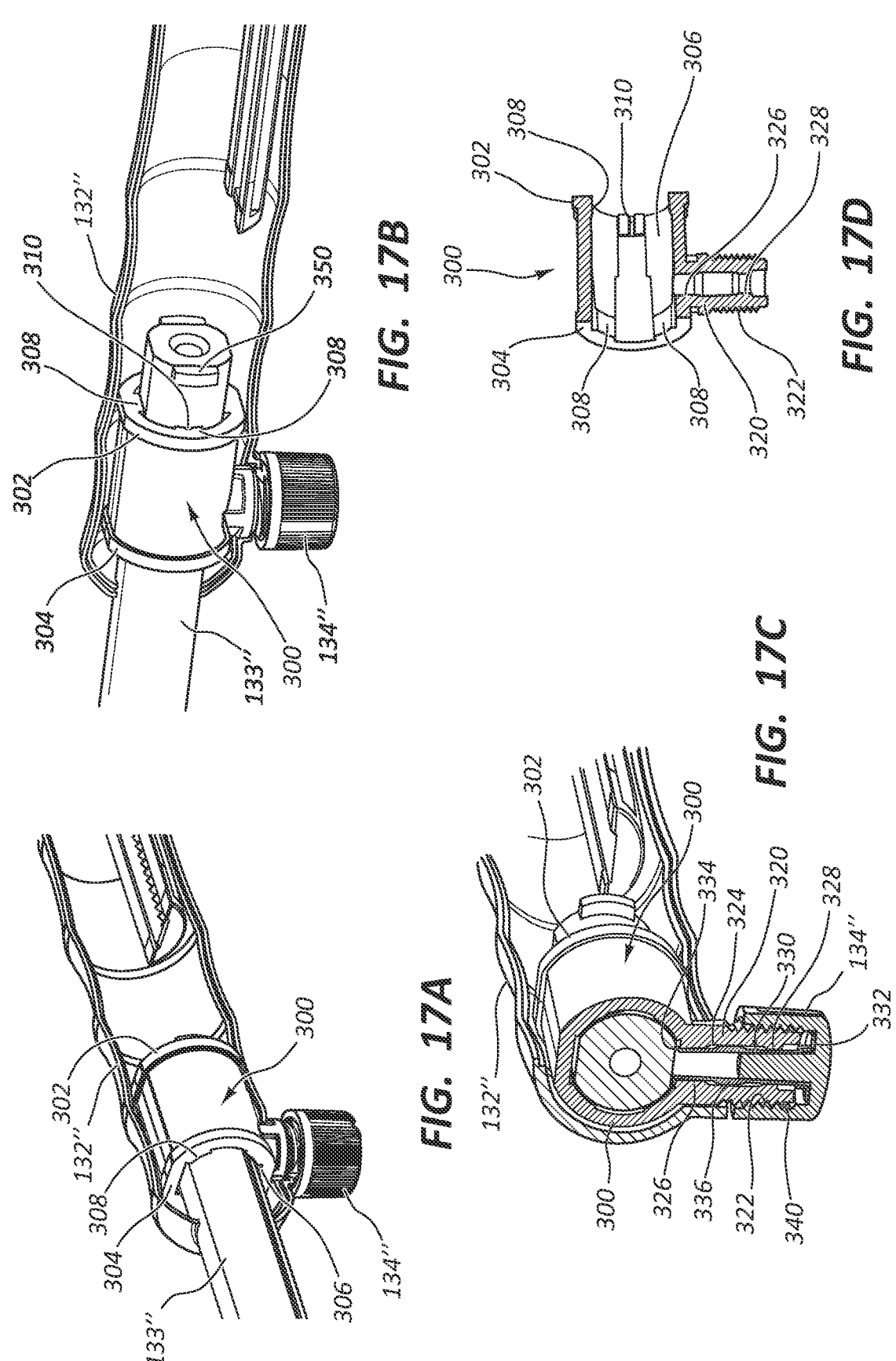
FIG. 17A illustrates a breakaway view of the thumbscrew from a distal view.
FIG. 17B illustrates a breakaway view of the thumbscrew from a proximal view.
FIG. 17C illustrates a breakaway cross-sectional view of the thumbscrew and a bushing.
FIG. 17D illustrates a cross-sectional view of the bushing of FIGS. 17A-17C.

FIG. 17A illustrates a breakaway view of the thumbscrew 134" from a distal view. FIG. 17B illustrates a breakaway view of the thumbscrew 134" from a proximal view. A bushing 300 disposed within the slide handle 132" may be disposed around the piston 133'. The bushing 300 and the piston 133" may be coaxial with the slide handle 132" and may be disposed along the longitudinal axis of the slide handle 132". The bushing 300 may be configured to stabilize the piston 133" and to keep the piston 133" in coaxial alignment with the slide handle 132". The bushing 300 extends between a proximal end 302 and a distal end 304 and defines an internal lumen 306 configured to be disposed around the piston 133". The bushing 300 may further include a plurality of pads 308 that project radially inward from the internal lumen 306 and the pads 308 may engage with the piston 133" to create a tight fit and/or to maintain the coaxial alignment of the piston 133" and the slide handle 132". The pads 308 are not configured to prevent longitudinal movement of the piston 133" but to create a minimal clearance fit to prevent or minimize the piston 133" from moving out of alignment with the slide handle 132". Thus, the pads 308 are configured to stabilize the piston 133" in coaxial alignment including during longitudinal displacement of the piston 133". The pads 308 on the distal end 304 are shown in the view of FIG. 17A and the pads 308 on the proximal end are shown in the view of FIG. 17B. In some embodiments, there may be four pads 308 on the proximal end 302 and four pads 308 on the distal end. However, there may be more or less than four pads 308 on each end. In some embodiments, there may be an unequal numbers of pads 308 on the proximal end 302 compared to the distal end 304.

In some embodiments the pads 308 are equally spaced around the internal circumference of the internal lumen 306. In some embodiments, the pads 308 on the proximal end 302 and the pads 308 on the distal end 304 may be misaligned with each other. In some embodiments, the pads 308 on the proximal end 302 and the pads 308 on the distal end 304 may be aligned with each other.

In some of the embodiments, such as illustrated in FIG. 17B, some of the pads 308 may include a groove 310 that is centrally disposed on the pad 308. The groove 310 is configured to enable a low clearance fit between the pad 308 and the piston 133" around the majority of the circumference of the piston 133" while also allowing increased tolerance along parting lines or other features of the piston 133", for example to allow greater tolerance for flashing on the piston 133" or other manufacturing artifacts or features.

In some embodiments, such as illustrated in FIG. 17B, the piston 133" may further include a plurality of projections 350 that project radially outward from a proximal end of the piston 133". The projections 350 are configured to interact with the bushing 300 and prevent the piston 133" from moving too far in a distal direction relative to the slide handle 132".

FIG. 17C illustrates a breakaway cross-sectional view of the thumbscrew 134" and the bushing 300. The bushing 300 may further include a projection 320 that extends from an outer surface of the bushing 300. The projection may include threads 322 configured to interacts with corresponding threads 340 on the thumbscrew 134". The projection 320 may further include an internal lumen 324, such as a lumen centrally disposed within the projection 320. The internal lumen 324 of the projection may be in communication with the lumen 306 of the bushing 300. The internal lumen 324 may include multiple narrow portions. For example, internal lumen 324 may include a first narrow portion 326 that is proximal of the internal lumen 306 of the bushing 300 and a second narrow portion 328 that is distal of the internal lumen 306 of the bushing 300.

The thumbscrew 134" may further include a locking feature 330. The locking feature may include a first end 332 and a second end 334, the first end 332 may be coupled to an internal surface of the thumbscrew 134". The second end 334 is engagable with the piston 133". In use, a user may turn the thumbscrew to advance the second end 334 of the locking feature into engagement with the piston 133". When the locking feature 330 is thus engaged with the piston 133", the locking feature 330 may prevent or minimize movement of the piston 133" relative to the slide handle 132". The user may turn the thumbscrew in a opposite direction to retract the locking feature 330 and disengage the locking feature 330 from the piston 133" to facilitate longitudinal displacement of the piston 133" relative to the slide handle 132".

The locking feature 330 may further include a bulbous or bulging feature 336 that bulges or projects radially outward from the locking feature 330. The bulging feature 336 may be disposed between the first narrow portion 326 and the second narrow portion 328 of the internal lumen 324 of the projection 320. The bulging feature 336 may thus tend to maintain the thumbscrew 134" coupled to the bushing 300 and to the slide handle 132" and prevent accidental uncoupling of the thumbscrew 134" from the bushing 300 and the slide handle 132". In other words, the thumbscrew 134" may be rotated such that the thumbscrew 134" allows for longitudinal displacement of the piston 133" and the bulging feature 336 prevents the thumbscrew 134" from falling off or otherwise decoupling from the entire assembly. The thumbscrew 134" may be uncoupled from the bushing and the slide handle 132" if a sufficient force is applied to displace the bulging feature 336 past the second narrow portion 328 of the internal lumen 324 of the projection 320.

FIG. 17D illustrates a perspective cross-sectional view of the bushing 300. The pads 308 are shown extending in the longitudinal direction of the bushing 300. The length of the pads in the longitudinal direction may vary. In some embodiments, the pads 308 interface with the piston 133", but the internal lumen 306 does not directly contact or interface with the fixed piston. Groove 310 of some of the pads 308 extend longitudinally as well.

Figure 18:
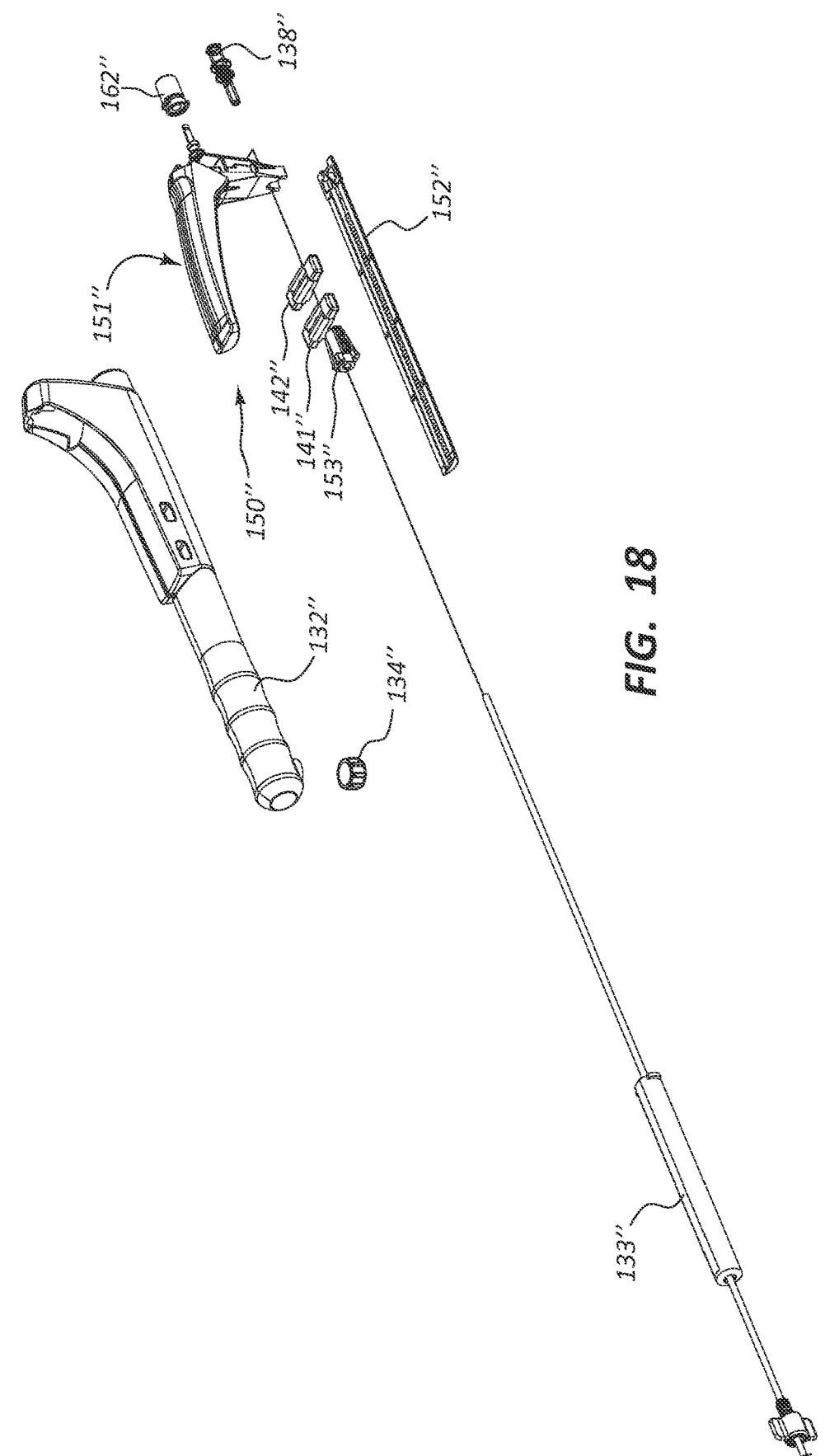
FIG. 18 illustrates an exploded view of a housing assembly of FIG. 17.

FIG. 18 illustrates an exploded view of the housing assembly 130". The handle assembly 150" includes an actuator or lever 151", a track 152", and a sheath adapter 153". The actuator 151" is configured to pivot about a pivot point when actuated. A spring 145" may engage with the actuator 151" when the actuator 151" is depressed. The spring 145" may return the actuator 151" to its unpivoted position when the actuator 151" is no longer depressed by a user. As the actuator 151" is depressed and pivots, it engages with the track 152" and moves the track 152" proximally (unless the first and second safety buttons 141" and 142" are not pressed, as is discussed below). The track 152" may be engaged with the sheath adapter 153". As the track 152" proximally retracts, the sheath adapter 153" may thus follow with it. The sheath adapter 153" is fixedly coupled to the outer sheath 116". Proximal movement of the sheath adapter 153" therefore results in proximal movement of the outer sheath 116". Partial retraction of the sheath adapter 153" results in deployment of the distal half of the prosthesis. Complete retraction of the sheath adapter 153" results in full deployment of the prosthesis.

Figure 19:
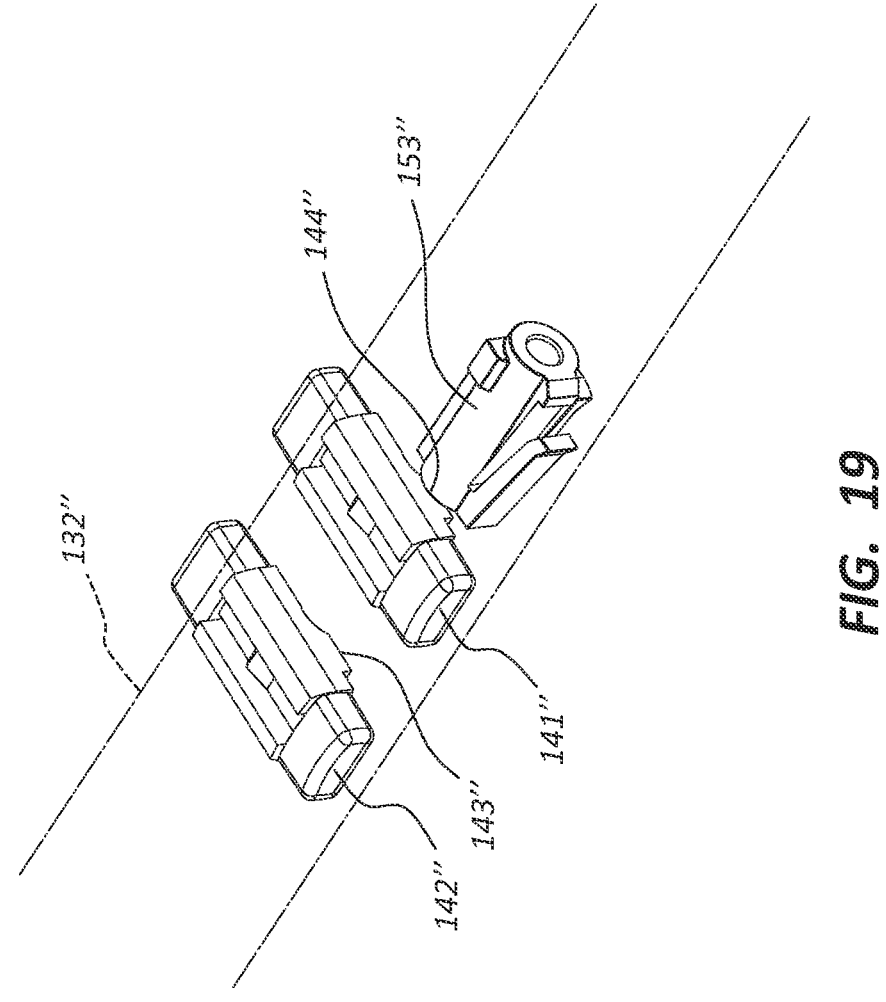
FIG. 19 illustrates a perspective view of the safety buttons of FIG. 17.
Figure 20:
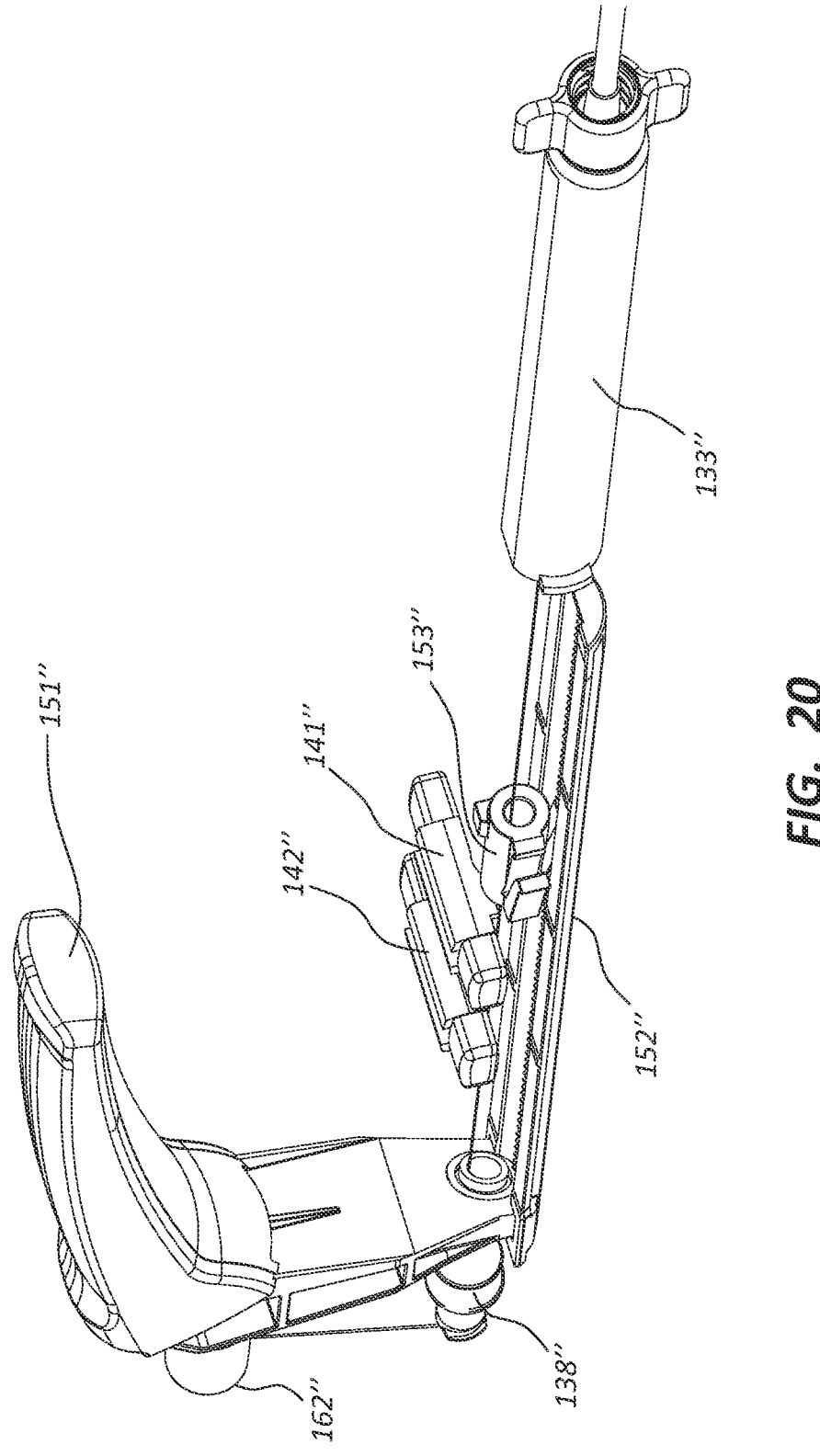
FIG. 20 illustrates a breakaway view of the safety button of FIG. 17.

The first and second safety buttons 141" and 142" illustrated in FIGS. 19 and 20 are non-detachable push buttons configured to interact with the sheath adapter 153" when the first and second safety buttons 141" and 142" are not pressed. The first and second safety buttons 141" and 142" each include a protrusion 143" and 144", respectively. The protrusions 143" and 144" are configured to interact with the sheath adapter 153". When the first safety button 141" is not pressed, the sheath adapter 153" is unable to move proximally when the actuator 151" is depressed. When the first safety button 111" is pressed, the first safety button 141" slides in a direction orthogonal to the longitudinal direction of the prosthesis delivery device 100" and the protrusion 143" is configured to no longer engage with the sheath adapter 153". With the first safety button 141" engaged, the sheath adapter 153" is able to move proximally when the actuator 151" is depressed and until the sheath adapter 153" engages with the protrusion 144" of the second safety button 142" (which corresponds to the deployment of the distal half of the prosthesis). When the second safety button 142" is pressed, the second safety button 142" slides in a direction orthogonal to the longitudinal direction of the prosthesis delivery device 100" and the protrusion 144" is configured to no longer engage with the sheath adapter 153". With the second safety button 142" pressed, the sheath adapter 153" is able to move proximally when the actuator 151" is able to fully proximally retract (which corresponds to the full deployment of the prosthesis).

One of the benefits of the illustrated embodiments of the prosthesis delivery device 100 is that the handle assembly 150 may be completely operated with one hand, including removal of the first and second safety tabs 141 and 142.

In the illustrated embodiment, it is not possible to depress the actuator 151 when the first safety tab 141 is in place. In other embodiments, the handle assembly 150 may be configured such that depressing the actuator 151 is possible, but has no effect unless the first safety tab 141 is removed. Additionally, in the illustrated embodiment of FIG. 15, the track 152 is configured so that each full ratchet of the track 152 by the actuator 151 retracts the outer sheath 116 about 1 cm. In some embodiments, the track 152 may be modified to provide much smaller increments of movement over an entire depression of the actuator 151 or to provide small movements of the outer sheath 116 as the actuator 151 is partially depressed. For example, a full ratchet may retract the outer sheath 116 about 1 cm, but partial ratchet may move the outer sheath 116 in 2 mm increments until it reaches a full ratchet and movement of 1 cm. This may enable the user to have greater precision when deploying the prosthesis. It should be understood that the illustrated embodiment is just one approach to proximally retracting the outer sheath 116. One of ordinary skill in the art, with the benefit of this disclosure, would understand that a number of approaches may be used for retracting the outer sheath 116.

It should be understood that the prosthesis delivery device 100 will normally be supplied as a kit with a prosthesis, such as the prosthesis 200, loaded into the prosthesis pod 117; however, that may not always be the case.

The prosthesis delivery devices disclosed herein may be used for a variety of procedures. For example, any time it is desirable to deploy a prosthesis in two stages, but with only one-hand, then it may be beneficial to use the prosthesis delivery devices disclosed herein. For example, the prosthesis delivery devices disclosed herein may be used for draining one lumen of a patient into another lumen of a patient, such as, for example, transgastric or transduodenal drainage of a pancreatic pseudocyst, of a biliary tract, of a gallbladder. An access port may be created with the tip electrode between a first lumen of the patient and a second lumen of the patient. The first lumen may be the gastrointestinal tract (for example, the esophagus, stomach, pylorus, or bowel) of the patient. The second lumen may be the gallbladder, a pancreatic cyst, a biliary tract, or some other lumen that needs drainage.

For example, draining a target structure of a patient may include introducing an echoendoscope into the gastrointestinal tract of the patient with the terminal end in the vicinity of the target structure. A guidewire may be inserted through the working channel of the echoendoscope into the target structure. The delivery catheter assembly 110 (with a prosthesis loaded into the prosthesis pod 117) may then be slid over the guidewire and into the working channel of the echoendoscope. Alternatively, a guidewire may not be present, and instead the location of the terminal end of the echoendoscope is sufficiently precisely positioned near the target structure so as to guide placement of the delivery catheter assembly 110. The housing assembly 130 may be secured to the echoendoscope. The tip electrode 170 may extend just beyond the terminal end of the echoendoscope. When using the housing assembly 130, with one-hand, while watching the endoscope video screen, the user may unlock the handle 132, energize the tip electrode 170 (such as by depressing a foot pedal connected to the electrosurgical power generator), slide the handle 132 distally until the target structure has been penetrated and an access port created. The electrode tip 170 may then be deenergized (such as by releasing the foot pedal). The handle 132 may then be locked in place with the same hand. With the same hand as before, the first safety tab 141 may be removed from the housing assembly 130. With the same hand the actuator 151 may then be depressed and thereby deploy the distal end of the prosthesis in the target structure of the patient. With the same hand, the housing assembly 130 may be retracted proximally (and thereby the entire delivery catheter assembly 110 and the partially deployed prosthesis) to confirm visually either endoscopically, fluoroscopically, or via ultrasound that the distal end of the prosthesis is secured against the tissue wall inside the target structure. With the same hand the second safety tab 142 may then be removed from the housing assembly 130. With the same hand the actuator 151 may again be depressed and thereby deploy the proximal end of the prosthesis in the gastrointestinal tract of the patient. With the same hand the handle 132 may be unlocked and proximally retracted to withdraw the electrode tip 170 from the target structure. The prosthesis, such as the prosthesis 200, can now allow drainage of the target structure.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, only a portion of a method described herein may be a separate method. Stated otherwise, some methods may include only a portion of the steps described in a more detailed method.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of this disclosure.

The invention claimed is:

1. A method of deploying a prosthesis in a patient, the method comprising:

introducing a delivery catheter assembly into a working channel of an echoendoscope, wherein the delivery catheter assembly comprises: an outer sheath; a prosthesis loaded into a prosthesis pod region of the outer sheath, wherein the prosthesis has a proximal end and a distal end; and at least one marker visible on the outer sheath to indicate a position of the delivery catheter for deployment of the prosthesis;

inserting with one-hand the prosthesis pod region at least partially into a target structure through an access port in the target structure;

ascertaining the position of the delivery catheter including the prosthesis relative to the target structure by visually observing the at least one marker before deployment of the prosthesis; and after ascertaining the position of the delivery catheter relative to the target structure of the prosthesis by visually observing the at least one marker, actuating with the same one-hand an actuator of a housing assembly operably connected to the delivery catheter assembly to deploy the prosthesis with the distal end of the prosthesis within the target structure and the proximal end of the prosthesis outside the target structure, wherein actuating comprises depressing the actuator one or more times to deploy the prosthesis.

2. The method of claim 1, wherein inserting the prosthesis pod region comprises creating the access port in the target structure.

3. The method of claim 2, wherein the delivery catheter assembly further comprises a tip electrode, and creating the access port comprises:

energizing the tip electrode;

pushing with the same one-hand the tip electrode into the target structure; and de-energizing the tip electrode after penetrating the target structure.

4. The method of claim 1, wherein ascertaining the position of the delivery catheter including the prosthesis comprises observing the at least one marker endoscopically or fluoroscopically.

5. The method of claim 1, further comprising engaging with the same one-hand a safety button on the housing assembly, prior to actuating with the same one-hand the actuator to deploy the prosthesis.

6. The method of claim 1, further comprising coupling the delivery catheter assembly with the working channel of the echoendoscope via a rotatable luer lock adapter.

7. The method of claim 1, wherein introducing the delivery catheter assembly comprises sliding the delivery catheter assembly over a guidewire inserted into the working channel of the echoendoscope.

8. The method of claim 1, wherein the proximal end and the distal end of the prosthesis each comprises a flare that is situated outside the access port when the prosthesis is deployed.

9. The method of claim 1, wherein the housing assembly comprises a slide assembly, and further comprising adjusting a position of the delivery catheter assembly relative to the echoendoscope while visually observing the at least one marker.

10. The method of claim 1, wherein a first marker of the at least one marker indicates a position of the proximal end of the prosthesis.

11. A method for draining a first lumen of a patient into a second lumen of the patient, comprising:

inserting a delivery catheter assembly into a working channel of an echoendoscope, wherein the delivery catheter assembly comprises: an outer sheath; a prosthesis loaded into the outer sheath in a prosthesis pod region having a proximal end and a distal end; and at least one marker visible on the outer sheath to indicate a position of the delivery catheter for deployment of the prosthesis;

advancing a tip of the delivery catheter assembly into the first lumen within the patient, wherein the first lumen has a first lumen wall;

pushing with one-hand the tip of the delivery catheter assembly and at least the distal end of the prosthesis pod region through the first lumen wall and into the second lumen;

confirming the position of the delivery catheter including the prosthesis pod region relative to the first lumen wall by visually observing the at least one marker before deployment of the prosthesis;

adjusting with the same one-hand a position of the delivery catheter assembly so that the proximal end of the prosthesis pod region is in the first lumen and the distal end of the prosthesis pod region is in the second lumen; and after visually observing the at least one marker, actuating with the same one-hand an actuator of a housing assembly operably connected to the delivery catheter assembly and thereby deploying the prosthesis, wherein actuating comprises depressing the actuator a plurality of times to deploy the prosthesis.

12. The method of claim 11, wherein the tip comprises an electrode and further comprising energizing the electrode prior to pushing the tip through the first lumen wall and then de-energizing the electrode after penetrating the second lumen.

13. The method of claim 11, wherein confirming the position of the delivery catheter including the prosthesis pod region comprises observing the at least one marker endoscopically or fluoroscopically.

14. The method of claim 11, further comprising engaging with the same one-hand a safety button on the housing assembly, prior to actuating with the same one-hand the actuator to deploy the prosthesis.

15. The method of claim 11, wherein the first lumen is a gastrointestinal tract of the patient.

16. The method of claim 11, wherein the second lumen is a gallbladder, a biliary tract, a pancreatic cyst, or a pancreatic pseudocyst in the patient.

17. The method of claim 11, further comprising coupling the delivery catheter assembly with the working channel of the echoendoscope prior to pushing the tip through the first lumen wall.

18. The method of claim 11, wherein the proximal end and the distal end of the prosthesis comprises a flared proximal end and a flared distal end that are situated within the first lumen and the second lumen, respectively, upon deployment of the prosthesis.

19. The method of claim 11, wherein a first marker of the at least one marker indicates a position of the proximal end of the prosthesis rod region.

20. A prosthesis deployment device comprising:

an elongate delivery catheter assembly configured for electrosurgery and also configured to retain and deploy a prosthesis, and comprising: an outer sheath; a prosthesis pod region within the outer sheath configured to receive the prosthesis in elongated form; and at least one marker visible on the outer sheath and configured to provide visibility of the outer sheath including prosthesis pod region to a user before deployment of the prosthesis;

a housing assembly operably coupled to the delivery catheter assembly and configured to connect to an electrosurgical power generator, wherein the housing assembly comprises an actuator configured to displace a portion of the delivery catheter assembly to deploy the prosthesis, upon actuation, wherein the actuator is configured for one-handed operation, wherein the actuator is configured to be depressed and pivot upon actuation, and wherein the actuator returns to its unpivoted position when the actuator is no longer depressed.

* * * * *